(12) United States Patent
Hill et al.

(10) Patent No.: US 10,470,830 B2
(45) Date of Patent: Nov. 12, 2019

(54) SYSTEMS AND METHODS FOR INSTRUMENT BASED INSERTION ARCHITECTURES

(71) Applicant: Auris Health, Inc., Redwood City, CA (US)

(72) Inventors: Aren Calder Hill, Mountain View, CA (US); Travis Michael Schuh, Los Altos, CA (US); Nicholas J. Eyre, Sunnyvale, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/215,208

(22) Filed: Dec. 10, 2018

(65) Prior Publication Data

US 2019/0175287 A1 Jun. 13, 2019

Related U.S. Application Data

(60) Provisional application No. 62/597,385, filed on Dec. 11, 2017.

(51) Int. Cl.
*A61B 34/30* (2016.01)
*A61B 90/00* (2016.01)
(Continued)

(52) U.S. Cl.
CPC ............. *A61B 34/30* (2016.02); *A61B 90/37* (2016.02); *A61B 2017/00725* (2013.01);
(Continued)

(58) Field of Classification Search
None
See application file for complete search history.

(56) References Cited

U.S. PATENT DOCUMENTS 2,556,601 A 6/1951 Schofield
2,566,183 A 8/1951 Forss
(Continued)

FOREIGN PATENT DOCUMENTS

CN 101500470 8/2009
CN 102665590 9/2012
(Continued)

OTHER PUBLICATIONS

International Search Report and Written Opinion dated Feb. 14, 2019 in application No. PCT/US2018/064789.
(Continued)

*Primary Examiner* — Brian T Gedeon
(74) *Attorney, Agent, or Firm* — Knobbe, Martens, Olson & Bear, LLP

(57) ABSTRACT

Systems, devices and methods are provided in which an instrument can translate along an insertion axis. Rather than relying primarily on a robotic arm for instrument insertion, the instruments described herein have novel instrument based insertion architectures that allow portions of the instruments themselves to translate along an insertion axis. For example, an instrument can comprise a shaft, an end effector on a distal end of the shaft, and a handle coupled to the shaft. The architecture of the instrument allows the shaft to translate relative to the handle along an axis of insertion. The translation of the shaft does not interfere with other functions of the instrument, such as end effector actuation.

27 Claims, 28 Drawing Sheets

(51) Int. Cl.
    *A61B 34/00*     (2016.01)
    *A61B 17/00*     (2006.01)
    *A61B 34/20*     (2016.01)

(52) U.S. Cl.
    CPC . *A61B 2034/2065* (2016.02); *A61B 2034/301* (2016.02); *A61B 2034/302* (2016.02); *A61B 2034/303* (2016.02); *A61B 2034/715* (2016.02); *A61B 2090/364* (2016.02)

(56) References Cited

U.S. PATENT DOCUMENTS

| | | |
|---|---|---|
| 2,730,699 A | 1/1956 | Gratian |
| 2,884,808 A | 5/1959 | Mueller |
| 3,294,183 A | 12/1966 | Riley et al. |
| 3,472,083 A | 10/1969 | Schnepel |
| 3,513,724 A | 5/1970 | Box |
| 3,595,074 A | 7/1971 | Johnson |
| 3,734,207 A | 5/1973 | Fishbein |
| 4,141,245 A | 2/1979 | Brandstetter |
| 4,241,884 A | 12/1980 | Lynch |
| 4,243,034 A | 1/1981 | Brandt |
| 4,351,493 A | 9/1982 | Sonnek |
| 4,357,843 A | 11/1982 | Peck et al. |
| 4,384,493 A | 5/1983 | Grunbaum |
| 4,507,026 A | 3/1985 | Lund |
| 4,530,471 A | 7/1985 | Inoue |
| 4,555,960 A | 12/1985 | King |
| 4,688,555 A | 8/1987 | Wardle |
| 4,745,908 A | 5/1988 | Wardle |
| 4,784,150 A | 11/1988 | Voorhies et al. |
| 4,857,058 A | 8/1989 | Payton |
| 4,907,168 A | 3/1990 | Boggs |
| 4,945,790 A | 8/1990 | Golden |
| 5,207,128 A | 5/1993 | Albright |
| 5,234,428 A | 8/1993 | Kaufman |
| 5,256,150 A | 10/1993 | Quiachon et al. |
| 5,277,085 A | 1/1994 | Tanimura et al. |
| 5,350,101 A | 9/1994 | Godlewski |
| 5,426,687 A | 6/1995 | Goodall et al. |
| 5,507,725 A | 4/1996 | Savage et al. |
| 5,524,180 A | 6/1996 | Wang et al. |
| 5,559,294 A | 9/1996 | Hoium et al. |
| 5,767,840 A | 6/1998 | Selker |
| 5,779,623 A | 7/1998 | Bonnell |
| 5,792,135 A | 8/1998 | Madhani et al. |
| 5,855,583 A | 1/1999 | Wang et al. |
| 5,921,968 A | 7/1999 | Lampropoulos et al. |
| 5,967,934 A | 10/1999 | Ishida et al. |
| 6,084,371 A | 7/2000 | Kress et al. |
| 6,154,000 A | 11/2000 | Rastegar et al. |
| 6,171,234 B1 | 1/2001 | White et al. |
| 6,185,478 B1 | 2/2001 | Koakutsu et al. |
| 6,272,371 B1 | 8/2001 | Shlomo |
| 6,289,579 B1 | 9/2001 | Viza et al. |
| 6,394,998 B1 | 5/2002 | Wallace et al. |
| 6,401,572 B1 | 6/2002 | Provost |
| 6,436,107 B1 | 8/2002 | Wang et al. |
| 6,487,940 B2 | 12/2002 | Hart et al. |
| 6,491,701 B2 | 12/2002 | Tierney et al. |
| 6,676,684 B1 | 1/2004 | Morley et al. |
| 6,695,818 B2 | 2/2004 | Wollschlager |
| 6,726,675 B1 | 4/2004 | Beyar |
| 6,786,896 B1 | 9/2004 | Madhani et al. |
| 6,827,712 B2 | 12/2004 | Tovey et al. |
| 7,044,936 B2 | 5/2006 | Harding |
| 7,172,580 B2 | 2/2007 | Hruska et al. |
| 7,276,044 B2 | 10/2007 | Ferry et al. |
| 7,615,042 B2 | 11/2009 | Beyar et al. |
| 7,635,342 B2 | 12/2009 | Ferry et al. |
| 7,766,856 B2 | 8/2010 | Ferry et al. |
| 7,938,809 B2 | 5/2011 | Lampropoulos et al. |
| 7,974,674 B2 | 7/2011 | Hauck et al. |
| 7,998,020 B2 | 8/2011 | Kidd et al. |
| 8,052,636 B2 | 11/2011 | Moll et al. |
| 8,157,308 B2 | 4/2012 | Pedersen |
| 8,182,415 B2 | 5/2012 | Larkin et al. |
| 8,277,417 B2 | 10/2012 | Fedinec et al. |
| 8,291,791 B2 | 10/2012 | Light et al. |
| 8,671,817 B1 | 3/2014 | Bogusky |
| 8,720,448 B2 | 5/2014 | Reis et al. |
| 8,746,252 B2 | 6/2014 | McGrogan et al. |
| 8,961,533 B2 | 2/2015 | Stahler et al. |
| 8,968,333 B2 | 3/2015 | Yu et al. |
| 9,095,362 B2 | 8/2015 | Dachs et al. |
| 9,173,713 B2 | 11/2015 | Hart et al. |
| 9,204,933 B2 | 12/2015 | Reis et al. |
| 9,220,567 B2 | 12/2015 | Sutherland et al. |
| 9,326,822 B2 | 5/2016 | Lewis et al. |
| 9,333,041 B2 | 5/2016 | Yeung et al. |
| 9,408,669 B2 | 8/2016 | Kokish et al. |
| 9,452,018 B2 | 9/2016 | Yu |
| 9,457,168 B2 | 10/2016 | Moll et al. |
| 9,474,569 B2 | 10/2016 | Manzo et al. |
| 9,498,601 B2 | 11/2016 | Tanner et al. |
| 9,504,604 B2 | 11/2016 | Alvarez |
| 9,561,083 B2 | 2/2017 | Yu et al. |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,889,568 B2 | 2/2018 | Kilroy et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,011,018 B2 | 7/2018 | McGrogan et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,052,155 B2 | 8/2018 | Morley et al. |
| 10,080,576 B2 | 9/2018 | Romo et al. |
| 10,136,959 B2 | 11/2018 | Mintz et al. |
| 10,143,360 B2 | 12/2018 | Roelle et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,871 B2 | 3/2019 | Mirbagheri et al. |
| 10,258,333 B2 | 4/2019 | Shelton et al. |
| 10,258,359 B2 | 4/2019 | Kapadia et al. |
| 10,258,421 B2 | 4/2019 | Lohmeier et al. |
| 2001/0042643 A1 | 11/2001 | Krueger et al. |
| 2002/0045905 A1 | 4/2002 | Gerbi et al. |
| 2002/0098938 A1 | 7/2002 | Milbourne et al. |
| 2002/0100254 A1 | 8/2002 | Dharssi |
| 2002/0107573 A1 | 8/2002 | Steinberg |
| 2002/0117017 A1 | 8/2002 | Bernhardt et al. |
| 2002/0161355 A1 | 10/2002 | Wollschlager |
| 2002/0161426 A1 | 10/2002 | Lancea |
| 2002/0177789 A1 | 11/2002 | Ferry et al. |
| 2003/0056561 A1 | 3/2003 | Butscher et al. |
| 2004/0015053 A1 | 1/2004 | Bieger |
| 2004/0152972 A1 | 8/2004 | Hunter |
| 2004/0243147 A1 | 12/2004 | Lipow |
| 2005/0004579 A1 | 1/2005 | Schneider et al. |
| 2005/0183532 A1 | 8/2005 | Najaf et al. |
| 2005/0222554 A1 | 10/2005 | Wallace et al. |
| 2006/0111692 A1 | 5/2006 | Hlavka et al. |
| 2006/0146010 A1 | 7/2006 | Schneider |
| 2006/0201688 A1 | 9/2006 | Jenner et al. |

(56) References Cited

U.S. PATENT DOCUMENTS

| | | |
|---|---|---|
| 2006/0229587 A1 | 10/2006 | Beyar et al. |
| 2006/0237205 A1 | 10/2006 | Sia et al. |
| 2007/0000498 A1 | 1/2007 | Glynn et al. |
| 2007/0013336 A1 | 1/2007 | Nowlin et al. |
| 2007/0060879 A1 | 3/2007 | Weitzner et al. |
| 2007/0100254 A1 | 5/2007 | Murakami |
| 2007/0112355 A1 | 5/2007 | Salahieh |
| 2007/0119274 A1 | 5/2007 | Devengenzo et al. |
| 2007/0149946 A1 | 6/2007 | Viswanathan |
| 2007/0191177 A1 | 8/2007 | Nagai et al. |
| 2007/0245175 A1 | 10/2007 | Zheng et al. |
| 2007/0299427 A1 | 12/2007 | Yeung et al. |
| 2008/0039255 A1 | 2/2008 | Jinno et al. |
| 2008/0046122 A1 | 2/2008 | Manzo et al. |
| 2008/0065103 A1 | 3/2008 | Cooper et al. |
| 2008/0147011 A1 | 6/2008 | Urmey |
| 2008/0177285 A1 | 7/2008 | Brock et al. |
| 2008/0214925 A1 | 9/2008 | Wilson et al. |
| 2008/0243064 A1 | 10/2008 | Stahler et al. |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0302200 A1 | 12/2008 | Tobey |
| 2009/0082722 A1 | 3/2009 | Munger et al. |
| 2009/0098971 A1 | 4/2009 | Ho et al. |
| 2009/0105645 A1 | 4/2009 | Kidd et al. |
| 2009/0171371 A1 | 7/2009 | Nixon |
| 2009/0247944 A1 | 10/2009 | Kirschenman et al. |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0130923 A1 | 5/2010 | Cleary et al. |
| 2010/0130987 A1 | 5/2010 | Wenderow et al. |
| 2010/0175701 A1 | 7/2010 | Reis et al. |
| 2010/0204646 A1 | 8/2010 | Plicchi et al. |
| 2010/0210923 A1 | 8/2010 | Li et al. |
| 2010/0248177 A1 | 9/2010 | Mangelberger et al. |
| 2011/0015484 A1 | 1/2011 | Alvarez et al. |
| 2011/0015648 A1 | 1/2011 | Alvarez et al. |
| 2011/0028991 A1 | 2/2011 | Ikeda et al. |
| 2011/0130718 A1 | 6/2011 | Kidd et al. |
| 2011/0147030 A1 | 6/2011 | Blum et al. |
| 2011/0152880 A1 | 6/2011 | Alvarez et al. |
| 2011/0238083 A1 | 9/2011 | Moll et al. |
| 2011/0261183 A1 | 10/2011 | Ma et al. |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2012/0071821 A1 | 3/2012 | Yu |
| 2012/0071894 A1 | 3/2012 | Tanner et al. |
| 2012/0071895 A1 | 3/2012 | Stahler et al. |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0232476 A1 | 9/2012 | Bhat et al. |
| 2012/0239012 A1 | 9/2012 | Laurent et al. |
| 2012/0277730 A1 | 11/2012 | Salahieh |
| 2012/0283747 A1 | 11/2012 | Popovic |
| 2013/0018400 A1 | 1/2013 | Milton et al. |
| 2013/0144116 A1 | 6/2013 | Cooper et al. |
| 2013/0231678 A1 | 9/2013 | Wenderow |
| 2013/0304084 A1 | 11/2013 | Beira et al. |
| 2013/0317519 A1 | 11/2013 | Romo et al. |
| 2013/0345519 A1 | 12/2013 | Piskun et al. |
| 2014/0000411 A1 | 1/2014 | Shelton, IV et al. |
| 2014/0069437 A1 | 3/2014 | Reis et al. |
| 2014/0142591 A1 | 5/2014 | Alvarez et al. |
| 2014/0166023 A1 | 6/2014 | Kishi |
| 2014/0171778 A1 | 6/2014 | Tsusaka |
| 2014/0222019 A1 | 8/2014 | Brudnick |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |
| 2014/0276935 A1 | 9/2014 | Yu |
| 2014/0276936 A1 | 9/2014 | Kokish et al. |
| 2014/0277334 A1 | 9/2014 | Yu et al. |
| 2014/0309649 A1 | 10/2014 | Alvarez et al. |
| 2014/0357984 A1 | 12/2014 | Wallace et al. |
| 2014/0364870 A1 | 12/2014 | Alvarez et al. |
| 2015/0051592 A1 | 2/2015 | Kintz |
| 2015/0090063 A1 | 4/2015 | Lantermann et al. |
| 2015/0119638 A1 | 4/2015 | Yu et al. |
| 2015/0133963 A1 | 5/2015 | Barbagli |
| 2015/0142013 A1 | 5/2015 | Tanner et al. |
| 2015/0148600 A1 | 5/2015 | Ashinuma et al. |
| 2015/0164594 A1 | 6/2015 | Romo et al. |
| 2015/0164596 A1 | 6/2015 | Romo |
| 2015/0182250 A1 | 7/2015 | Conlon et al. |
| 2015/0231364 A1 | 8/2015 | Blanchard |
| 2015/0327939 A1 | 11/2015 | Kokish et al. |
| 2015/0335480 A1 | 11/2015 | Alvarez et al. |
| 2015/0374445 A1 | 12/2015 | Gombert et al. |
| 2016/0000512 A1 | 1/2016 | Gombert et al. |
| 2016/0001038 A1 | 1/2016 | Romo et al. |
| 2016/0157945 A1 | 6/2016 | Madhani |
| 2016/0166234 A1 | 6/2016 | Zhang |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0331208 A1 | 11/2016 | Kikuchi et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0354582 A1 | 12/2016 | Yu et al. |
| 2016/0374541 A1 | 12/2016 | Agrawal et al. |
| 2017/0000573 A1 | 1/2017 | Millman et al. |
| 2017/0007337 A1 | 1/2017 | Dan |
| 2017/0007343 A1 | 1/2017 | Yu |
| 2017/0020615 A1 | 1/2017 | Koenig et al. |
| 2017/0071684 A1 | 3/2017 | Kokish et al. |
| 2017/0100199 A1 | 4/2017 | Yu et al. |
| 2017/0105804 A1 | 4/2017 | Yu |
| 2017/0119413 A1 | 5/2017 | Romo |
| 2017/0119481 A1 | 5/2017 | Romo et al. |
| 2017/0119484 A1 | 5/2017 | Tanner et al. |
| 2017/0151028 A1 | 6/2017 | Ogawa et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209672 A1 | 7/2017 | Hart et al. |
| 2017/0252540 A1 | 9/2017 | Weitzner et al. |
| 2017/0273749 A1 | 9/2017 | Grover et al. |
| 2017/0281049 A1 | 10/2017 | Yamamoto |
| 2017/0290631 A1 | 10/2017 | Lee et al. |
| 2017/0296784 A1 | 10/2017 | Kokish |
| 2017/0312481 A1 | 11/2017 | Covington et al. |
| 2017/0333679 A1 | 11/2017 | Jiang |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0042464 A1 | 2/2018 | Arai |
| 2018/0049792 A1 | 2/2018 | Eckert |
| 2018/0049794 A1 | 2/2018 | Swayze et al. |
| 2018/0049827 A1 | 2/2018 | Harris et al. |
| 2018/0056044 A1 | 3/2018 | Choi et al. |
| 2018/0110576 A1 | 4/2018 | Kopp |
| 2018/0140366 A1 | 5/2018 | Kapadia |
| 2018/0177383 A1 | 6/2018 | Noonan et al. |
| 2018/0177556 A1 | 6/2018 | Noonan et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0221096 A1 | 8/2018 | Yates et al. |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0296299 A1 | 10/2018 | Iceman |
| 2018/0311001 A1 | 11/2018 | Prisco |

(56) References Cited

U.S. PATENT DOCUMENTS

| | | |
|---|---|---|
| 2018/0325499 A1 | 11/2018 | Landey et al. |
| 2018/0325611 A1 | 11/2018 | Robinson et al. |
| 2018/0326181 A1 | 11/2018 | Kokish et al. |
| 2018/0333044 A1 | 11/2018 | Jenkins |
| 2018/0338805 A1 | 11/2018 | Morley et al. |
| 2018/0344319 A1 | 12/2018 | Shelton et al. |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0099227 A1 | 4/2019 | Rockrohr |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0142537 A1 | 5/2019 | Covington et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |

FOREIGN PATENT DOCUMENTS

| | | |
|---|---|---|
| DE | 19649082 | 1/1998 |
| DE | 102004020465 | 9/2005 |
| EP | 1 442 720 | 8/2004 |
| EP | 2 567 670 | 3/2013 |
| EP | 3 025 630 | 6/2016 |
| JP | 2009-139187 | 6/2009 |
| JP | 2010-046384 | 3/2010 |
| WO | WO 02/74178 | 9/2002 |
| WO | WO 07/146987 | 12/2007 |
| WO | WO 09/092059 | 7/2009 |
| WO | WO 11/005335 | 1/2011 |
| WO | WO 12/037506 | 3/2012 |
| WO | WO 13/179600 | 12/2013 |
| WO | WO 15/127231 | 8/2015 |
| WO | WO 17/0151993 | 9/2017 |

OTHER PUBLICATIONS

Mayo Clinic, Robotic Surgery, https://www.mayoclinic.org/tests-procedures/robotic-surgery/about/pac-20394974?p=1, downloaded from the internet on Jul. 12, 2018, 2 pp.

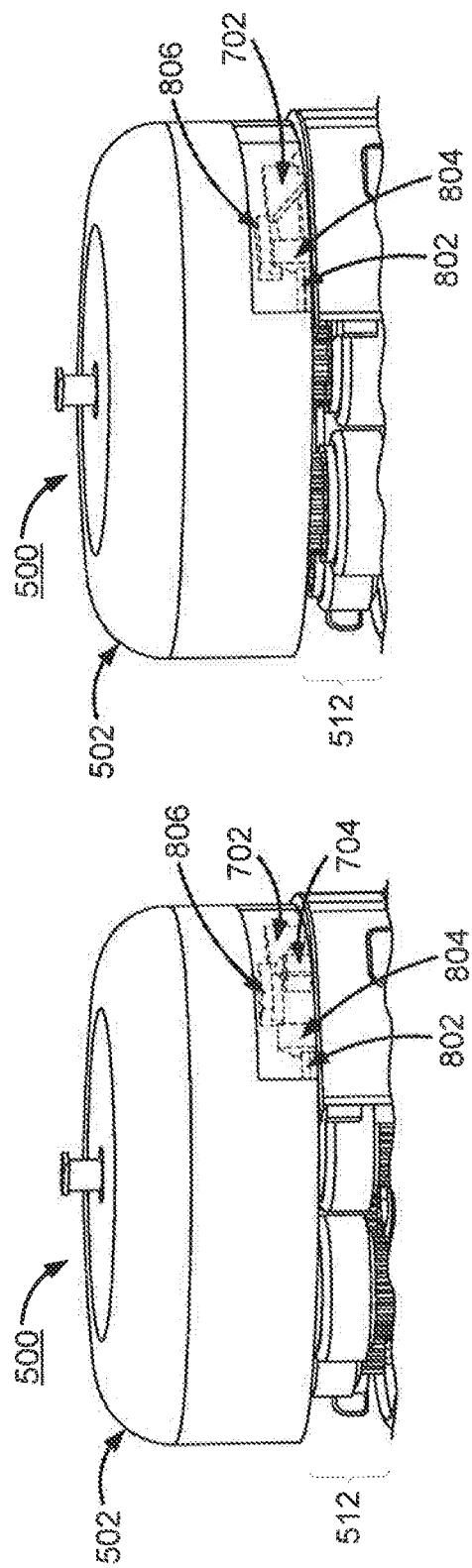

SYSTEMS AND METHODS FOR INSTRUMENT BASED INSERTION ARCHITECTURES

CROSS-REFERENCE TO RELATED APPLICATION(S)

This application claims the benefit of U.S. Provisional Application No. 62/597,385, filed Dec. 11, 2017, which is hereby incorporated by reference in its entirety.

TECHNICAL FIELD

The systems and methods disclosed herein are directed to medical instruments, and more particularly to surgical tools for use in various types of surgeries.

BACKGROUND

This description generally relates to medical instruments, and particularly to surgical tools for use in various types of surgeries, including laparoscopic, endoscopic, endoluminal and open surgeries.

Robotic technologies have a range of applications. In particular, robotic arms help complete tasks that a human would normally perform. For example, factories use robotic arms to manufacture automobiles and consumer electronics products. Additionally, scientific facilities use robotic arms to automate laboratory procedures such as transporting microplates. In the medical field, physicians have started using robotic arms to help perform surgical procedures.

In a surgical robotic system, a robotic arm is connected to an instrument device manipulator, e.g., at the end of the robotic arm, and is capable of moving the instrument device manipulator into any position within a defined work space. The instrument device manipulator can be detachably coupled to a surgical tool, such as a steerable catheter for endoscopic applications or any of a variety of laparoscopic and endoluminal instruments. The instrument device manipulator imparts motion from the robotic arm to control the position of the surgical tool, and it may also activate controls on the instrument, such as pull-wires to steer a catheter. Additionally, the instrument device manipulator may be electrically and/or optically coupled to the instrument to provide power, light, or control signals, and may receive data from the instrument such as a video stream from a camera on the instrument.

During use, a surgical tool is connected to the instrument device manipulator so that the instrument is away from a patient. The robotic arm then advances the instrument device manipulator and the instrument connected thereto towards a surgery site within the patient. In a laparoscopic procedure, the instrument is moved through a port in a body wall of the patient. The robotic arm is capable of manipulating the instrument in multiple degrees of freedom, including pitch, yaw and insertion. Typically, a robotic arm provides all of these degrees of freedom.

With respect to insertion, a robotic arm typically has a linear insertion axis to provide the insertion degree of freedom. Difficulties can arise when the robotic arm is responsible for the linear insertion of an instrument. In particular, the mass of the robotic arm (alone or in combination with an instrument) can lead to a heavy swung mass and reduce performance at shallow insertion depths. In addition, reliance on the robotic arm for insertion reduces the working space available for a surgeon or assistant during a robotic surgical procedure. Accordingly, there is a need to reduce reliance on the robotic arm when linearly inserting an instrument.

SUMMARY

Embodiments of the application are directed to systems, devices and methods that reduce reliance on a robotic arm when linearly inserting an instrument. In particular, the systems, devices and methods described herein relate to instruments having instrument based linear insertion architectures. For example, one or more instruments can be provided wherein a shaft of the instrument is capable of translation along an axis of insertion, thereby reducing reliance on the robotic arm for linear insertion. While in some embodiments, the robotic arm can still be used for linear insertion along with an instrument itself, in other embodiments, this motion is eliminated, thereby reducing the overall profile of the robot and minimizing swung mass at the end of the surgical robot arm.

In some embodiments, a medical device comprises a shaft, an end effector connected to the shaft, and a handle coupled to the shaft. The handle includes a first mechanical input and a second mechanical input. The first mechanical input is configured to cause actuation of the end effector, while the second mechanical input is configured to cause translation of the shaft relative to the handle. The actuation of the end effector is performed via a first actuation mechanism that is decoupled from a second actuation mechanism that causes the translation of the shaft relative to the handle. The first actuation mechanism can include a first cable that extends through a first set of pulleys, wherein manipulation of at least one pulley of the first set of pulleys via the first mechanical input causes a change of length of the first cable within the handle, thereby causing actuation of the end effector. The second actuation mechanism can include a second cable that engages a spool, wherein manipulation of the spool of the second set of pulleys via the second mechanical input causes the shaft to translate relative to the handle. The spool can be a capstan, such as a zero-walk capstan. The change of length of the first cable within the handle to cause actuation of the end effector is not affected by the second actuation mechanism that translates the shaft relative to the handle. In some instances, the cable of the first actuation mechanism extends from the proximal portion of the shaft, through the first set of pulleys and to the distal portion of the shaft. In other instances, the first actuation mechanism includes one or more cables that extend through a first set of pulleys, and the second actuation mechanism includes one or more cables and an insertion spool, wherein at least one or more cables of the first actuation mechanism terminates on the insertion spool.

In some embodiments, a medical system comprises a base, a tool holder coupled to the base, and an instrument. A robotic arm can be positioned between the base and the tool holder. The tool holder includes an attachment interface. The instrument comprises a shaft, an end effector and a handle having a reciprocal interface for attachment to the tool holder. The handle further includes a first mechanical input and a second mechanical input. The first mechanical input is configured to cause actuation of the end effector, while the second mechanical input is configured to cause translation of the shaft relative to the handle. The actuation of the end effector is performed via a first actuation mechanism that is decoupled from a second actuation mechanism that causes the translation of the shaft relative to the handle. In some instances, the first actuation mechanism includes a first cable that extends through a first set of pulleys, wherein manipulation of at least one pulley of the first set of pulleys via the first mechanical input causes a change of length of the first cable within the handle, thereby causing actuation of the end effector, and wherein the translation of the shaft relative to the handle is performed via the second actuation mechanism that includes a second cable that engages a spool, wherein manipulation of the spool via the second mechanical input causes the shaft to translate relative to the handle.

In some embodiments, a surgical method comprises providing an instrument configured for delivery through an incision or natural orifice of a patient to perform a surgical procedure at a surgical site. The instrument comprises a shaft, a handle coupled to the shaft, and an end effector extending from the shaft. The shaft is capable of translation relative to the handle. The actuation of the end effector is performed via a first actuation mechanism that is decoupled from a second actuation mechanism that causes the translation of the shaft relative to the handle. In some instances, the instrument includes a first actuation mechanism for actuating the end effector and a second actuation mechanism for translating the shaft relative to the handle, wherein the first actuation mechanism comprises a first set of pulleys and a first cable and the second actuation mechanism comprises a spool and a second cable.

In some embodiments, a surgical method comprises delivering an instrument through an incision or natural orifice of a patient to perform a surgical procedure at a surgical site. The instrument comprises a shaft, a handle coupled to the shaft, and an end effector extending from the shaft. The shaft is capable of translation relative to the handle. The actuation of the end effector is performed via a first actuation mechanism that is decoupled from a second actuation mechanism that causes the translation of the shaft relative to the handle. In some instances, the instrument includes a first actuation mechanism for actuating the end effector and a second actuation mechanism for translating the shaft relative to the handle, wherein the first actuation mechanism comprises a first set of pulleys and a first cable and the second actuation mechanism comprises a spool and a second cable.

BRIEF DESCRIPTION OF DRAWINGS

FIGS. 8A and 8B illustrate a process of engaging and disengaging a surgical tool from a sterile adapter, according to one embodiment.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

I. Surgical Robotic System

Figure 1A:
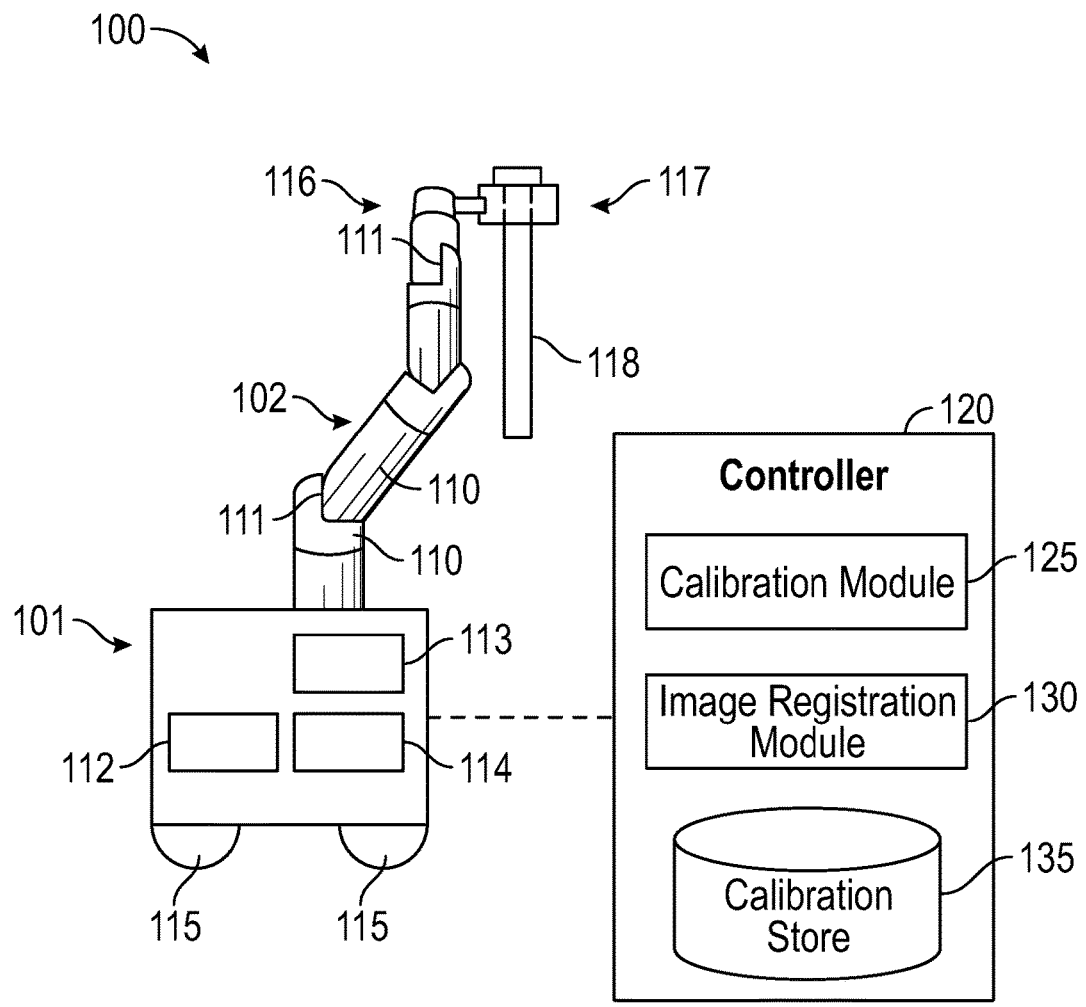
FIG. 1A illustrates a surgical robotic system, according to one embodiment.
Figure 1B:
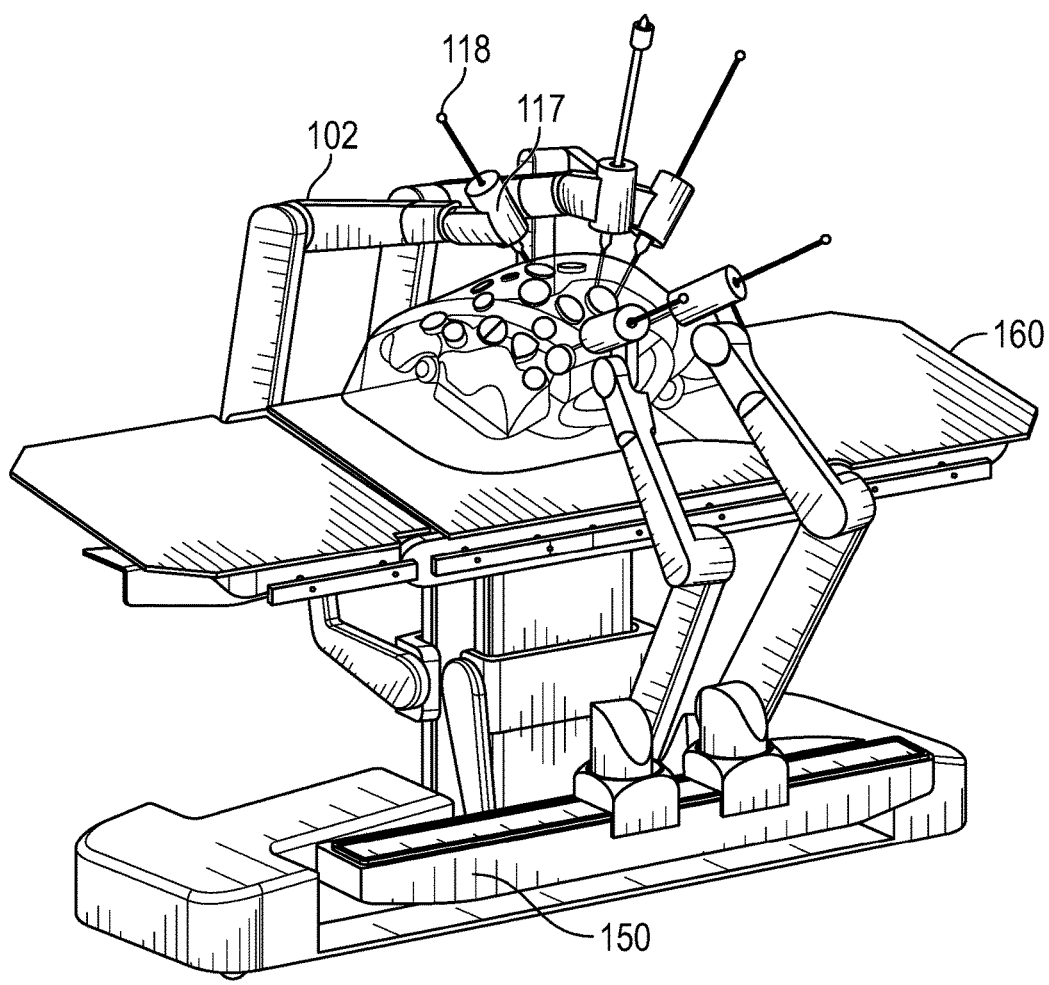
FIG. 1B illustrates a surgical robotic system, according to an alternative embodiment.

FIG. 1A illustrates an embodiment of a surgical robotic system 100. The surgical robotic system 100 includes a base 101 coupled to one or more robotic arms, e.g., robotic arm 102. The base 101 is communicatively coupled to a command console, which is further described herein with reference to FIG. 2. The base 101 can be positioned such that the robotic arm 102 has access to perform a surgical procedure on a patient, while a user such as a physician may control the surgical robotic system 100 from the comfort of the command console. In some embodiments, the base 101 may be coupled to a surgical operating table or bed for supporting the patient. For example, in some embodiments, a base 101 that is coupled to a robotic arm 102 can be coupled to a bed via one or more rails that extend along the bed (as shown in FIG. 1B). Though not shown in FIG. 1A for purposes of clarity, in some embodiments, the base 101 may include subsystems such as control electronics, pneumatics, power sources, optical sources, and the like. The robotic arm 102 includes multiple arm segments 110 coupled at joints 111, which provides the robotic arm 102 multiple degrees of freedom, e.g., seven degrees of freedom corresponding to seven arm segments. The base 101 may contain a source of power 112, pneumatic pressure 113, and control and sensor electronics 114—including components such as a central processing unit, data bus, control circuitry, and memory—and related actuators such as motors to move the robotic arm 102. The electronics 114 in the base 101 may also process and transmit control signals communicated from the command console.

In some embodiments, the base 101 includes wheels 115 to transport the surgical robotic system 100. Mobility of the surgical robotic system 100 helps accommodate space constraints in a surgical operating room as well as facilitate appropriate positioning and movement of surgical equipment. Further, the mobility allows the robotic arms 102 to be configured such that the robotic arms 102 do not interfere with the patient, physician, anesthesiologist, or any other equipment. During procedures, a user may control the robotic arms 102 using control devices such as the command console.

In some embodiments, the robotic arm 102 includes set up joints that use a combination of brakes and counter-balances to maintain a position of the robotic arm 102. The counter-balances may include gas springs or coil springs. The brakes, e.g., fail safe brakes, may include mechanical and/or electrical components. Further, the robotic arms 102 may be gravity-assisted passive support type robotic arms.

Each robotic arm 102 may be coupled to an instrument device manipulator (IDM) 117 using a mechanism changer interface (MCI) 116. The IDM 117 can serve as a tool holder. In some embodiments, the IDM 117 can be removed and replaced with a different type of IDM, for example, a first type of IDM that manipulates an endoscope can be replaced with a second type of IDM that manipulates a laparoscope. The MCI 116 includes connectors to transfer pneumatic pressure, electrical power, electrical signals, and optical signals from the robotic arm 102 to the IDM 117. The MCI 116 can be a set screw or base plate connector. The IDM 117 manipulates surgical tools such as the instrument 118 using techniques including direct drive, harmonic drive, geared drives, belts and pulleys, magnetic drives, and the like. The MCI 116 is interchangeable based on the type of IDM 117 and can be customized for a certain type of surgical procedure. The robotic arm 102 can include joint level torque sensing and a wrist at a distal end.

The tool or instrument 118 can comprise a laparoscopic, endoscopic and/or endoluminal instrument that is capable of performing a procedure at a surgical site of a patient. In some embodiments, the instrument 118 comprises a laparoscopic instrument insertable into an incision of a patient. The laparoscopic instrument can comprise a rigid, semi-rigid or flexible shaft. When designed for laparoscopy, the distal end of the shaft may be connected to an end effector that may comprise, for example, a wrist, a grasper, scissors or other surgical tool. In some embodiments, the instrument 118 comprises an endoscopic surgical tool that is inserted into the anatomy of a patient to capture images of the anatomy (e.g., body tissue). In some embodiments, the endoscopic instrument comprises a tubular and flexible shaft. The endoscope includes one or more imaging devices (e.g., cameras or sensors) that capture the images. The imaging devices may include one or more optical components such as an optical fiber, fiber array, or lens. The optical components move along with the tip of the instrument 118 such that movement of the tip of the instrument 118 results in changes to the images captured by the imaging devices. In some embodiments, the instrument 118 comprises an endoluminal instrument insertable through a natural orifice of a patient, such as a bronchoscope or urethroscope. The endoluminal instrument can comprise a tubular and flexible shaft. When designed for endoluminal surgery, the distal end of the shaft may be connected to an end effector that may comprise, for example, a wrist, a grasper, scissors, or other surgical tool.

In some embodiments, robotic arms 102 of the surgical robotic system 100 manipulate the instrument 118 using elongate movement members. The elongate movement members may include pull-wires, also referred to as pull or push wires, cables, fibers, or flexible shafts. For example, the robotic arms 102 actuate multiple pull-wires coupled to the instrument 118 to deflect the tip of the instrument 118. The pull-wires may include both metallic and non-metallic materials such as stainless steel, Kevlar, tungsten, carbon fiber, and the like. In some embodiments, the instrument 118 may exhibit nonlinear behavior in response to forces applied by the elongate movement members. The nonlinear behavior may be based on stiffness and compressibility of the instrument 118, as well as variability in slack or stiffness between different elongate movement members.

The surgical robotic system 100 includes a controller 120, for example, a computer processor. The controller 120 includes a calibration module 125, image registration module 130, and a calibration store 135. The calibration module 125 can characterize the nonlinear behavior using a model with piecewise linear responses along with parameters such as slopes, hystereses, and dead zone values. The surgical robotic system 100 can more accurately control an endoscope 118 by determining accurate values of the parameters. In some embodiments, some or all functionality of the controller 120 is performed outside the surgical robotic system 100, for example, on another computer system or server communicatively coupled to the surgical robotic system 100.

FIG. 1B illustrates a surgical robotic system, according to an alternative embodiment. Like the embodiment of the surgical robotic system in FIG. 1A, the surgical robotic system in FIG. 1B includes one or more robotic arms 102 having an IDM 117 and surgical tool or instrument 118 attached thereto. In the present embodiment, the one or more robotic arms 102 are attached to one or more adjustable rails 150 coupled to a patient platform 160 in the form of a bed. In the present embodiment, three robotic arms 102 are attached to an adjustable rail 150 on a first side of the patient platform 160, while two robotic arms 102 are attached to an adjustable rail 150 on a second side of the patient platform 160, thereby providing a system with bilateral arms.

II. Command Console

Figure 2:
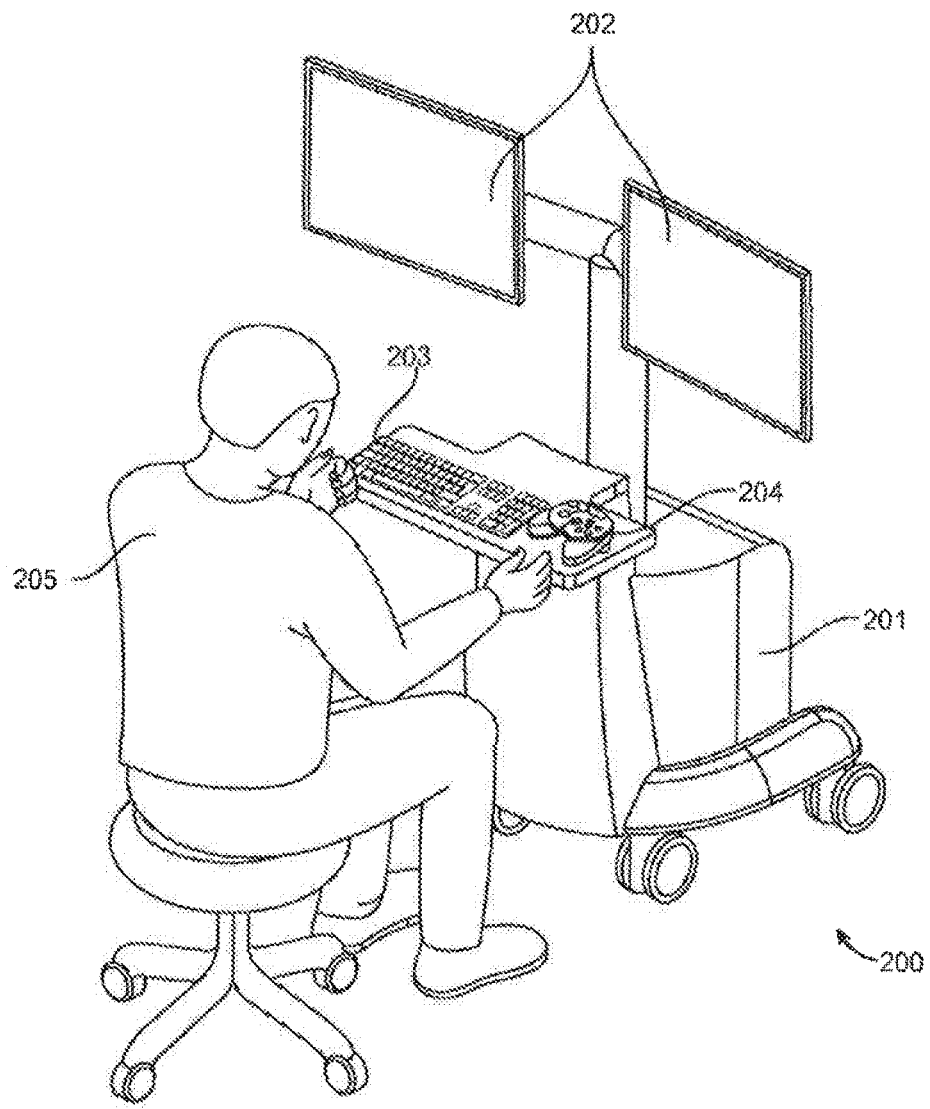
FIG. 2 illustrates a command console for a surgical robotic system, according to one embodiment.

FIG. 2 illustrates a command console 200 for a surgical robotic system 100 according to one embodiment. The command console 200 includes a console base 201, display modules 202, e.g., monitors, and control modules, e.g., a keyboard 203 and joystick 204. In some embodiments, one or more of the command module 200 functionality may be integrated into a base 101 of the surgical robotic system 100 or another system communicatively coupled to the surgical robotic system 100. A user 205, e.g., a physician, remotely controls the surgical robotic system 100 from an ergonomic position using the command console 200.

The console base 201 may include a central processing unit, a memory unit, a data bus, and associated data communication ports that are responsible for interpreting and processing signals such as camera imagery and tracking sensor data, e.g., from the instrument 118 shown in FIG. 1A. In some embodiments, both the console base 201 and the base 101 perform signal processing for load-balancing. The console base 201 may also process commands and instructions provided by the user 205 through the control modules 203 and 204. In addition to the keyboard 203 and joystick 204 shown in FIG. 2, the control modules may include other devices, for example, computer mice, track pads, trackballs, control pads, video game controllers, and sensors (e.g., motion sensors or cameras) that capture hand gestures and finger gestures.

The user 205 can control a surgical tool such as the instrument 118 using the command console 200 in a velocity mode or position control mode. In velocity mode, the user 205 directly controls pitch and yaw motion of a distal end of the instrument 118 based on direct manual control using the control modules. For example, movement on the joystick 204 may be mapped to yaw and pitch movement in the distal end of the instrument 118. The joystick 204 can provide haptic feedback to the user 205. For example, the joystick 204 vibrates to indicate that the instrument 118 cannot further translate or rotate in a certain direction. The command console 200 can also provide visual feedback (e.g., pop-up messages) and/or audio feedback (e.g., beeping) to indicate that the instrument 118 has reached maximum translation or rotation.

In position control mode, the command console 200 uses a three-dimensional (3D) map of a patient and pre-determined computer models of the patient to control a surgical tool, e.g., the instrument 118. The command console 200 provides control signals to robotic arms 102 of the surgical robotic system 100 to manipulate the instrument 118 to a target location. Due to the reliance on the 3D map, position control mode requires accurate mapping of the anatomy of the patient.

In some embodiments, users 205 can manually manipulate robotic arms 102 of the surgical robotic system 100 without using the command console 200. During setup in a surgical operating room, the users 205 may move the robotic arms 102, instruments 118, and other surgical equipment to access a patient. The surgical robotic system 100 may rely on force feedback and inertia control from the users 205 to determine appropriate configuration of the robotic arms 102 and equipment.

The display modules 202 may include electronic monitors, virtual reality viewing devices, e.g., goggles or glasses, and/or other means of display devices. In some embodiments, the display modules 202 are integrated with the control modules, for example, as a tablet device with a touchscreen. Further, the user 205 can both view data and input commands to the surgical robotic system 100 using the integrated display modules 202 and control modules.

The display modules 202 can display 3D images using a stereoscopic device, e.g., a visor or goggle. The 3D images provide an "endo view" (i.e., endoscopic view), which is a computer 3D model illustrating the anatomy of a patient. The "endo view" provides a virtual environment of the patient's interior and an expected location of an instrument 118 inside the patient. A user 205 compares the "endo view" model to actual images captured by a camera to help mentally orient and confirm that the instrument 118 is in the correct—or approximately correct—location within the patient. The "endo view" provides information about anatomical structures, e.g., the shape of an intestine or colon of the patient, around the distal end of the instrument 118. The display modules 202 can simultaneously display the 3D model and computerized tomography (CT) scans of the anatomy the around distal end of the instrument 118. Further, the display modules 202 may overlay pre-determined optimal navigation paths of the instrument 118 on the 3D model and CT scans.

In some embodiments, a model of the instrument 118 is displayed with the 3D models to help indicate a status of a surgical procedure. For example, the CT scans identify a lesion in the anatomy where a biopsy may be necessary. During operation, the display modules 202 may show a reference image captured by the instrument 118 corresponding to the current location of the instrument 118. The display modules 202 may automatically display different views of the model of the instrument 118 depending on user settings and a particular surgical procedure. For example, the display modules 202 show an overhead fluoroscopic view of the instrument 118 during a navigation step as the instrument 118 approaches an operative region of a patient.

III. Instrument Device Manipulator

Figure 3:
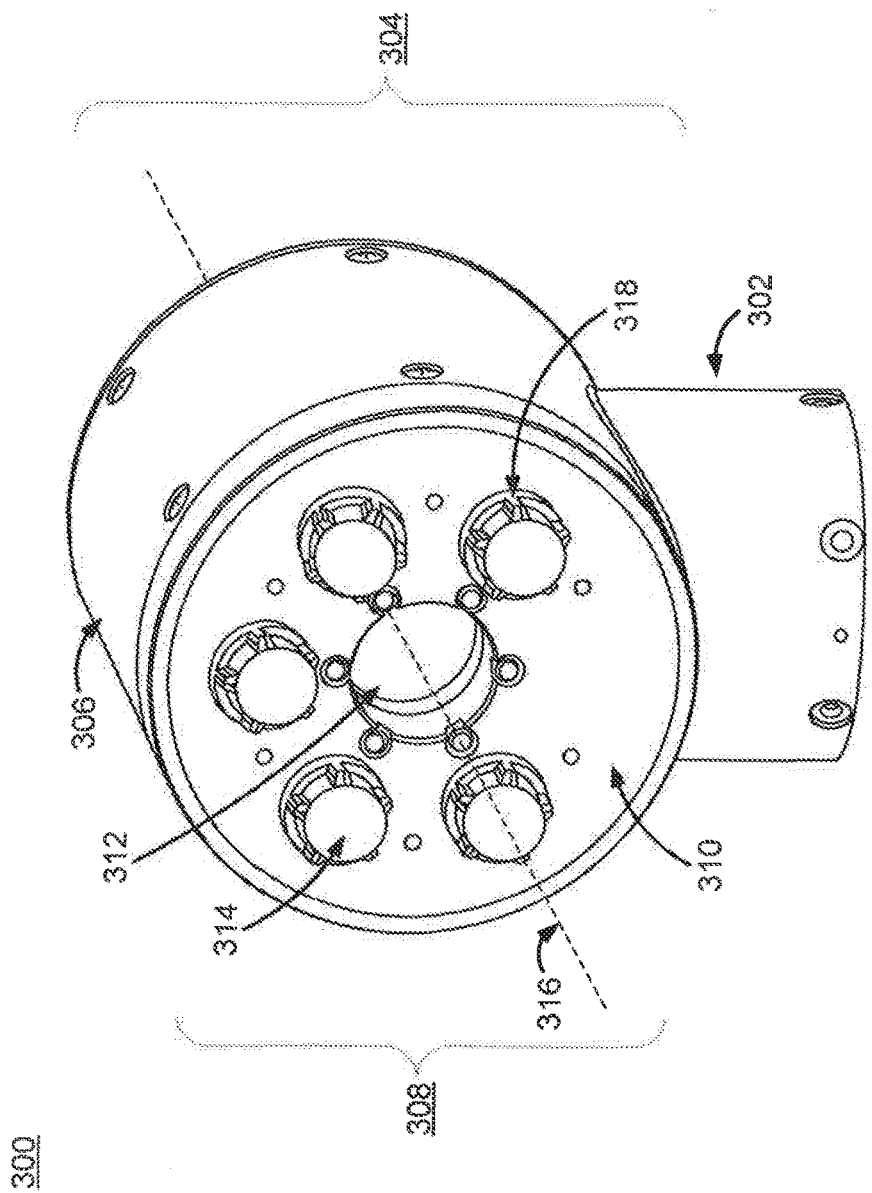
FIG. 3 illustrates a perspective view of an instrument device manipulator for a surgical robotic system, according to one embodiment.
Figure 4:
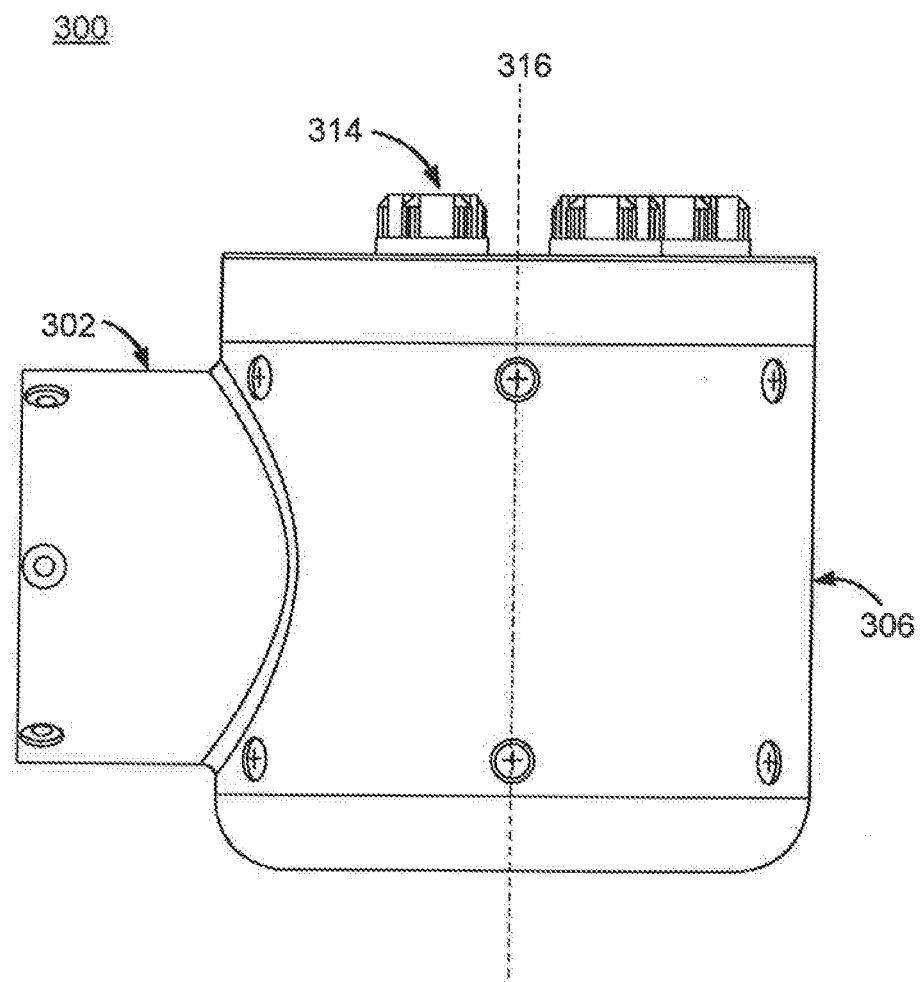
FIG. 4 illustrates a side view of the instrument device manipulator of FIG. 3, according to one embodiment.

FIG. 3 illustrates a perspective view of an instrument device manipulator (IDM) 300 for a surgical robotic system, and FIG. 4 is a side view of the IDM 300, according to one embodiment. The IDM 300 is configured to attach a surgical tool or instrument to a robotic surgical arm in a manner that allows the surgical tool to be continuously rotated or "rolled" about an axis of the surgical tool. The IDM 300 includes a base 302 and a surgical tool holder assembly 304 coupled to the base. The surgical tool holder assembly 304 serves as a tool holder for holding an instrument 118. The surgical tool holder assembly 304 further includes an outer housing 306, a surgical tool holder 308, an attachment interface 310, a passage 312, and a plurality of torque couplers 314. In some embodiments, the passage 312 comprises a through bore that extends from one face of the IDM 300 to an opposing face of the IDM 300. The IDM 300 may be used with a variety of surgical tools (not shown in FIG. 3), which may include a handle and an elongated body (e.g., a shaft), and which may be for a laparoscope, an endoscope, or other types of end-effectors of surgical tools.

The base 302 removably or fixedly mounts the IDM 300 to a surgical robotic arm of a surgical robotic system. In the embodiment of FIG. 3, the base 302 is fixedly attached to the outer housing 306 of the surgical tool holder assembly 304. In alternative embodiments, the base 302 may be structured to include a platform which is adapted to rotatably receive the surgical tool holder 308 on the face opposite from the attachment interface 310. The platform may include a passage aligned with the passage 312 to receive the elongated body of the surgical tool and, in some embodiments, an additional elongated body of a second surgical tool mounted coaxially with the first surgical tool.

The surgical tool holder assembly 304 is configured to secure a surgical tool to the IDM 300 and rotate the surgical tool relative to the base 302. Mechanical and electrical connections are provided from the surgical arm to the base 302 and then to the surgical tool holder assembly 304 to rotate the surgical tool holder 308 relative to the outer housing 306 and to manipulate and/or deliver power and/or signals from the surgical arm to the surgical tool holder 308 and ultimately to the surgical tool. Signals may include signals for pneumatic pressure, electrical power, electrical signals, and/or optical signals.

The outer housing 306 provides support for the surgical tool holder assembly 304 with respect to the base 302. The outer housing 306 is fixedly attached to the base 302 such that it remains stationary relative to the base 302, while allowing the surgical tool holder 308 to rotate freely relative to the outer housing 306. In the embodiment of FIG. 3, the outer housing 306 is cylindrical in shape and fully circumscribes the surgical tool holder 308. The outer housing 306 may be composed of rigid materials (e.g., metals or hard plastics). In alternative embodiments, the shape of the housing may vary.

The surgical tool holder 308 secures a surgical tool to the IDM 300 via the attachment interface 310. The surgical tool holder 308 is capable of rotating independent of the outer housing 306. The surgical tool holder 308 rotates about a rotational axis 316, which co-axially aligns with the elongated body of a surgical tool such that the surgical tool rotates with the surgical tool holder 308.

The attachment interface 310 is a face of the surgical tool holder 308 that attaches to the surgical tool. The attachment interface 310 includes a first portion of an attachment mechanism that reciprocally mates with a second portion of the attachment mechanism located on the surgical tool, which will be discussed in greater detail with regards to FIGS. 8A and 8B. In some embodiments, the attachment interface 310 comprises a plurality of torque couplers 314 that protrude outwards from the attachment interface 310 and engage with respective instrument inputs on the surgical tool. In some embodiments, a surgical drape, coupled to a sterile adapter, may be used to create a sterile boundary between the IDM 300 and the surgical tool. In these embodiments, the sterile adapter may be positioned between the attachment interface 310 and the surgical tool when the surgical tool is secured to the IDM 300 such that the surgical drape separates the surgical tool and the patient from the IDM 300 and the surgical robotics system.

The passage 312 is configured to receive the elongated body of a surgical tool when the surgical tool is secured to the attachment interface 310. In the embodiment of FIG. 3, the passage 312 is co-axially aligned with the longitudinal axis of the elongated body of the surgical tool and the rotational axis 316 of the surgical tool holder 308. The passage 312 allows the elongated body of the surgical tool to freely rotate within the passage 312. This configuration allows the surgical tool to be continuously rotated or rolled about the rotational axis 316 in either direction with minimal or no restrictions.

The plurality of torque couplers 314 are configured to engage and drive the components of the surgical tool when the surgical tool is secured to the surgical tool holder 308. Each torque coupler 314 is inserted into a respective instrument input located on the surgical tool. The plurality of torque couplers 314 may also serve to maintain rotational alignment between the surgical tool and the surgical tool holder 308. As illustrated in FIG. 3, each torque coupler 314 is shaped as a cylindrical protrusion that protrudes outwards from the attachment interface 310. Notches 318 may be arranged along the outer surface area of the cylindrical protrusion. In some embodiments, the arrangement of the notches 318 creates a spline interface. The instrument inputs on the surgical tool are configured to have a complementary geometry to the torque couplers 314. For example, while not shown in FIG. 3, the instrument inputs of the surgical tool may be cylindrical in shape and have a plurality of ridges that reciprocally mate with the plurality of notches 318 on each torque coupler 314 and thus impart a torque on the notches 318. In alternate embodiments, the top face of the cylindrical protrusion may include the plurality of notches 318 configured to mate with a plurality of ridges in respective instrument inputs. In this configuration, each torque coupler 314 fully engages with its respective instrument input.

Additionally, each torque coupler 314 may be coupled to a spring that allows the torque coupler to translate. In the embodiment of FIG. 3, the spring causes each torque coupler 314 to be biased to spring outwards away from the attachment interface 310. The spring is configured to create translation in an axial direction, i.e., protract away from the attachment interface 310 and retract towards the surgical tool holder 308. In some embodiments, each torque coupler 314 is capable of partially retracting into the surgical tool holder 308. In other embodiments, each torque coupler 314 is capable of fully retracting into the surgical tool holder 308 such that the effective height of each torque coupler is zero relative to the attachment interface 310. In the embodiment of FIG. 3, the translation of each torque coupler 314 is actuated by an actuation mechanism, which will be described in further detail with regards to FIGS. 7-8. In various embodiments, each torque coupler 314 may be coupled to a single spring, a plurality of springs, or a respective spring for each torque coupler.

In addition, each torque coupler 314 is driven by a respective actuator that causes the torque coupler to rotate in either direction. Thus, once engaged with an instrument input, each torque coupler 314 is capable of transmitting power to tighten or loosen pull-wires within a surgical tool, thereby manipulating a surgical tool's end-effectors. In the embodiment of FIG. 3, the IDM 300 includes five torque couplers 314, but the number may vary in other embodiments depending on the desired number of degrees of freedom for a surgical tool's end-effectors. In some embodiments, a surgical drape, coupled to a sterile adapter, may be used to create a sterile boundary between the IDM 300 and the surgical tool. In these embodiments, the sterile adapter may be positioned between the attachment interface 310 and the surgical tool when the surgical tool is secured to the IDM 300, and the sterile adapter may be configured to transmit power from each torque coupler 314 to the respective instrument input.

The embodiment of the IDM 300 illustrated in FIG. 3 may be used in various configurations with a surgical robotic system. The desired configuration may depend on the type of surgical procedure being performed on a patient or the type of surgical tool being used during the surgical procedure. For example, the desired configuration of the IDM 300 may be different for an endoscopic procedure than for a laparoscopic procedure.

In a first configuration, the IDM 300 may be removably or fixedly attached to a surgical arm such that the attachment interface 310 is proximal to a patient during the surgical procedure. In this configuration, hereinafter referred to as "front-mount configuration," the surgical tool is secured to the IDM 300 on a side proximal to the patient. A surgical tool for use with the front-mount configuration is structured such that the elongated body of the surgical tool extends from a side that is opposite of the attachment interface of the surgical tool. As a surgical tool is removed from the IDM 300 in a front-mount configuration, the surgical tool will be removed in a proximal direction to the patient.

In a second configuration, the IDM 300 may be removably or fixedly attached to a surgical arm such that the attachment interface 310 is distal to a patient during the surgical procedure. In this configuration, hereinafter referred to as "back-mount configuration," the surgical tool is secured to the IDM 300 on a side distal to the patient. A surgical tool for use with the back-mount configuration is structured such that the elongated body of the surgical tool extends from the attachment interface of the surgical tool. This configuration increases patient safety during tool removal from the IDM 300. As a surgical tool is removed from the IDM 300 in a back-mount configuration, the surgical tool will be removed in a distal direction from the patient.

In a third configuration, the IDM 300 may be removably or fixedly attached to a surgical arm such that at least a portion of the surgical tool is positioned above the IDM 300, similar to the configuration shown in FIG. 1A. In this configuration, hereinafter referred to as a "top" or "through" configuration, a shaft of the surgical tool extends downwardly through the IDM 300.

Certain configurations of a surgical tool may be structured such that the surgical tool can be used with an IDM in either a front-mount configuration or a back-mount configuration. In these configurations, the surgical tool includes an attachment interface on both ends of the surgical tool. For some surgical procedures, the physician may decide the configuration of the IDM depending on the type of surgical procedure being performed. For instance, the back-mount configuration may be beneficial for laparoscopic procedures wherein laparoscopic tools may be especially long relative to other surgical tools. As a surgical arm moves about during a surgical procedure, such as when a physician directs a distal end of the surgical tool to a remote location of a patient (e.g., a lung or blood vessel), the increased length of laparoscopic tools causes the surgical arm to swing about a larger arc. Beneficially, the back-mount configuration decreases the effective tool length of the surgical tool by receiving a portion of the elongated body through the passage 312 and thereby decreases the arc of motion required by the surgical arm to position the surgical tool.

Figure 5:
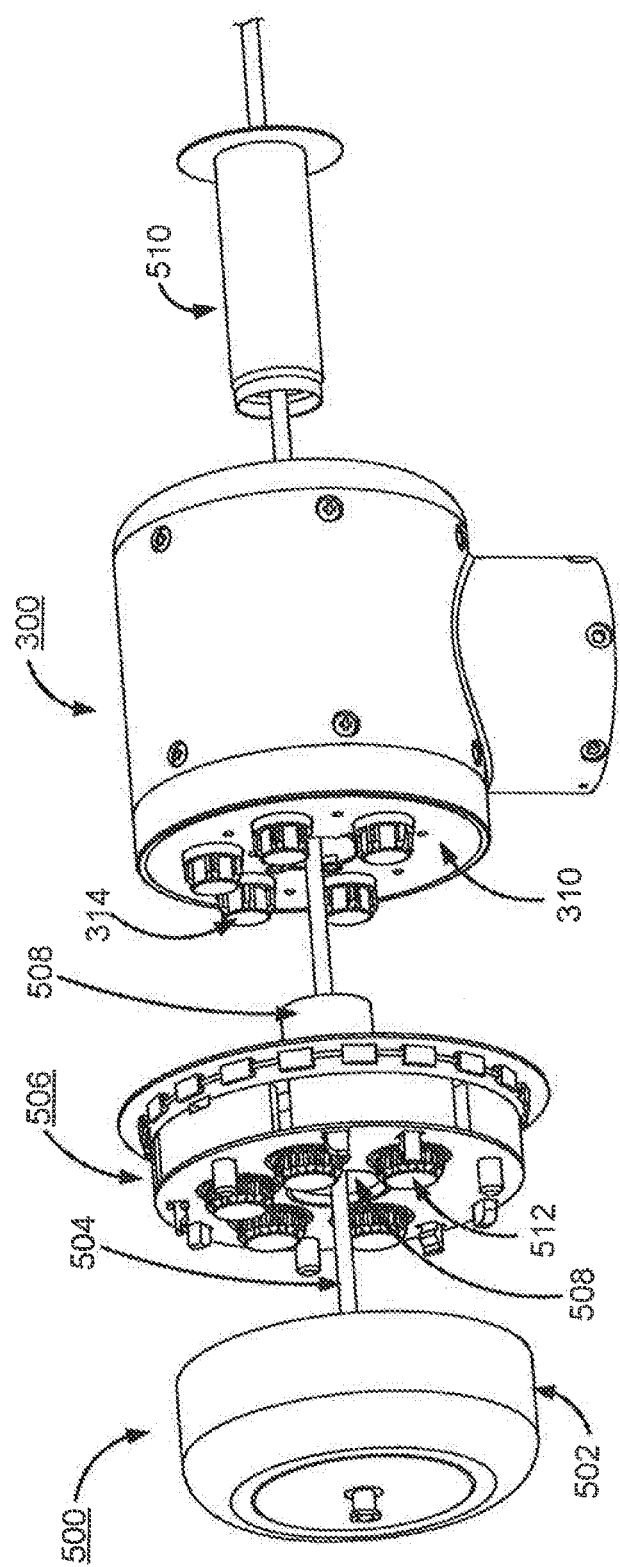
FIG. 5 illustrates a front-perspective exploded view of an example surgical tool secured to the instrument device manipulator of FIG. 3, according to one embodiment.
Figure 6:
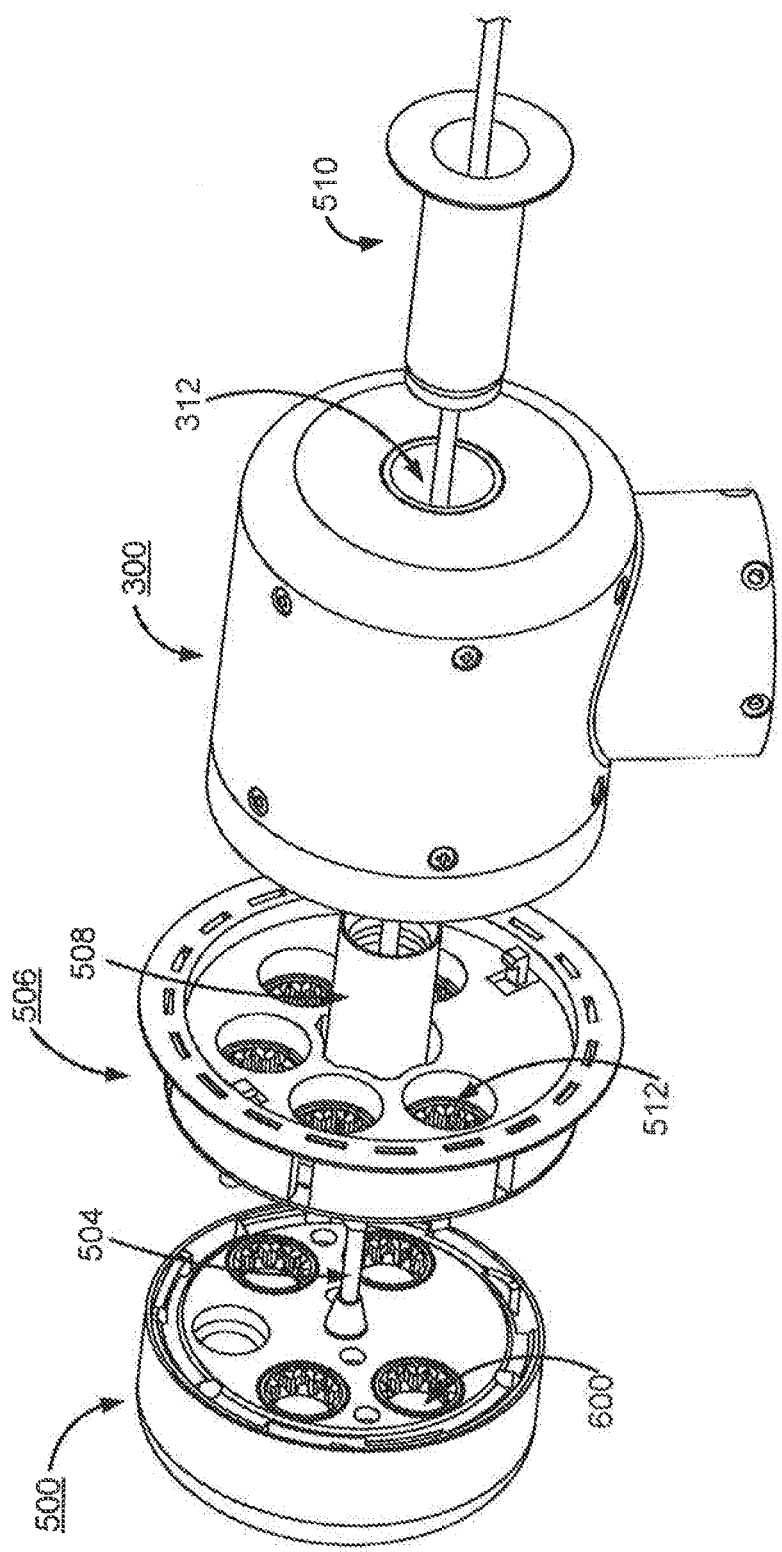
FIG. 6 illustrates a back-perspective exploded view of an example surgical tool secured to the instrument device manipulator of FIG. 3, according to one embodiment.

FIGS. 5-6 illustrate perspective exploded views of an example surgical tool 500 secured to the instrument device manipulator 300 of FIG. 3, according to one embodiment. The surgical tool 500 includes a housing 502, an elongated body 504, and a plurality of instrument inputs 600. As previously described, the elongated body 504 may be a laparoscope, an endoscope, or other surgical tool having end-effectors. As illustrated, the plurality of torque couplers 314 protrude outwards from the attachment interface 310 to engage with the instrument inputs 600 of the surgical tool. The structure of the instrument inputs 600 can be seen in FIG. 6, wherein the instrument inputs 600 have corresponding geometry to the torque couplers 314 to ensure secure surgical tool engagement.

During a surgical procedure, a surgical drape may be used to maintain a sterile boundary between the IDM 300 and an outside environment (i.e., an operating room). In the embodiments of FIGS. 5-6, the surgical drape comprises a sterile adapter 506, a first protrusion 508, and a second protrusion 510. While not shown in FIGS. 5-6, a sterile sheet is connected to the sterile adapter and the second protrusion and drapes around the IDM 300 to create the sterile boundary.

The sterile adapter 506 is configured to create a sterile interface between the IDM 300 and the surgical tool 500 when secured to the IDM 300. In the embodiment of FIGS. 5-6, the sterile adapter 506 has a disk-like geometry that covers the attachment interface 310 of the IDM 300. The sterile adapter 506 comprises a central hole 508 that is configured to receive the elongated body 504 of the surgical tool 500. In this configuration, the sterile adapter 506 is positioned between the attachment interface 310 and the surgical tool 500 when the surgical tool 500 is secured to the IDM 300, creating the sterile boundary between the surgical tool 500 and the IDM 300 and allowing the elongated body 504 to pass through the passage 312. In certain embodiments, the sterile adapter 506 may be capable of rotating with the surgical tool holder 308, transmitting the rotational torque from the plurality of torque couplers 314 to the surgical tool 500, passing electrical signals between the IDM 300 and the surgical tool 500, or some combination thereof.

In the embodiment of FIGS. 5-6, the sterile adapter 506 further comprises a plurality of couplers 512. A first side of a coupler 512 is configured to engage with a respective torque coupler 314 while a second side of a coupler 512 is configured to engage with a respective instrument input 600.

Similar to the structure of the plurality of torque couplers 314, each coupler 512 is structured as a cylindrical protrusion including a plurality of notches. Each side of the coupler 512 has complementary geometry to fully engage with the respective torque coupler 314 and the respective instrument input 600. In some embodiments, the one or more instrument inputs 600 are referred to as mechanical inputs. Each coupler 512 is configured to rotate in a clockwise or counter-clockwise direction with the respective torque coupler 314. This configuration allows each coupler 512 to transfer rotational torque from the plurality of torque couplers 314 of the IDM 300 to the plurality of instrument inputs 600 of the surgical tool 500, and thus control the end-effectors of the surgical tool 500.

The first protrusion 508 and the second protrusion 510 are configured to pass through the passage 312 of the IDM 300 and mate with each other inside the passage 312. Each protrusion 508, 510 is structured to allow the elongated body 504 to pass through the protrusion and thus the passage 312. The connection of the first protrusion 508 and the second protrusion 510 creates the sterile boundary between the IDM 300 and the outside environment (i.e., an operating room).

IV. Surgical Tool Disengagement

Figure 7:
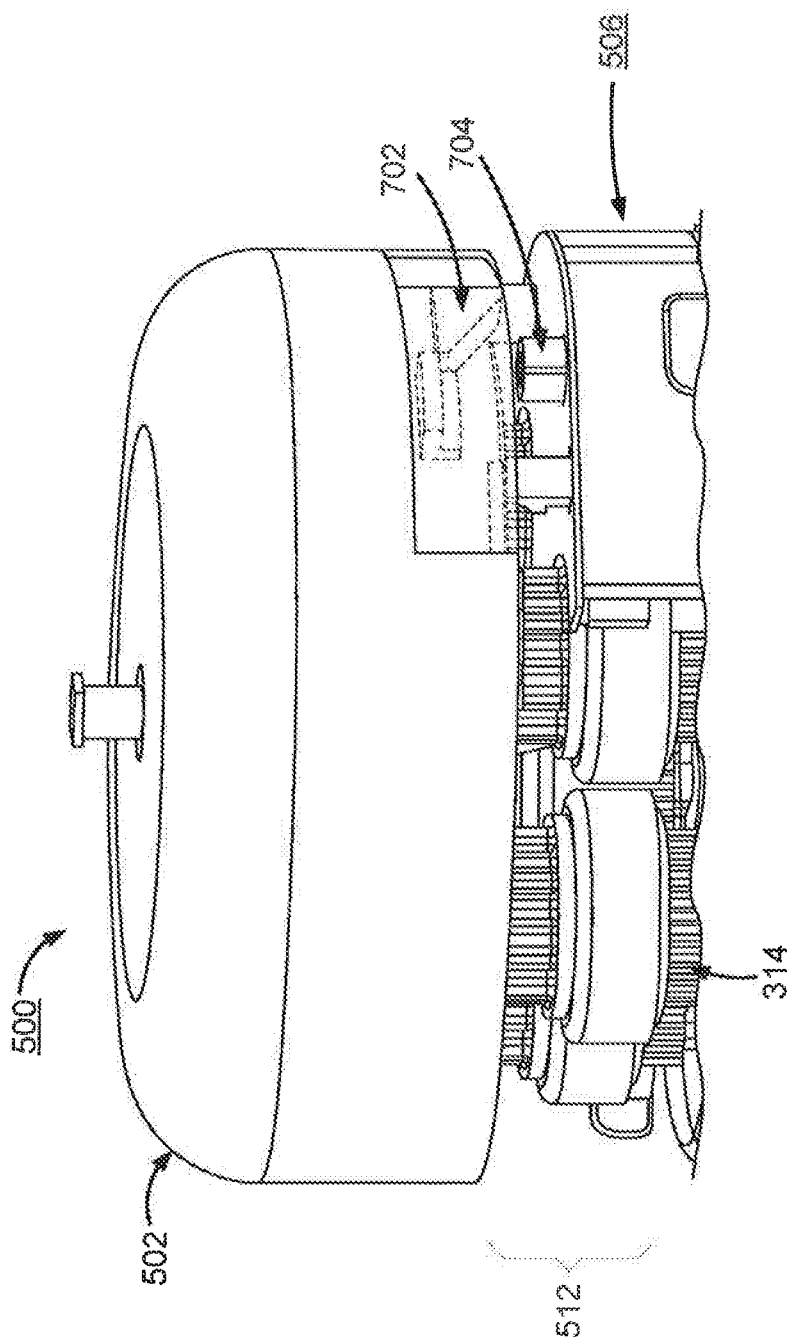
FIG. 7 illustrates a zoomed-in, perspective view of an actuation mechanism for engagement and disengagement of a surgical tool from a surgical tool holder, according to one embodiment.

FIG. 7 illustrates a zoomed-in, perspective view of an actuation mechanism for engagement and disengagement of a surgical tool 500 from a sterile adapter 506 of a surgical drape, according to one embodiment. Due to the configuration of the IDM 300 as described with regards to FIG. 3, the axis of surgical tool insertion into the patient during a surgical procedure is the same as the axis of surgical tool removal. To ensure patient safety during surgical tool removal, the surgical tool 500 can be de-articulated from the sterile adapter 506 and the IDM 300 before removing the surgical tool 500. In the embodiment of FIG. 7, the plurality of couplers 512 are configured to translate in an axial direction, i.e., protract away from and retract towards the sterile adapter 506. The translation of the plurality of couplers 512 is actuated by the actuation mechanism which ensures de-articulation of the surgical tool 500 by disengaging the plurality of couplers 512 from the respective instrument inputs 600. The actuation mechanism includes a wedge 702 and a pusher plate 704.

The wedge 702 is a structural component that activates the pusher plate 704 during the process of surgical tool disengagement. In the embodiment of FIG. 7, the wedge 702 is located within the housing 502 of the surgical tool 500 along the outer perimeter of the housing 502. As illustrated, the wedge 702 is oriented such that contact with the pusher plate 704 causes the pusher plate 704 to depress into the sterile adapter 506 if the housing 502 of the surgical tool 500 is rotated clockwise relative to the sterile adapter 506. In alternate embodiments, the wedge 702 may be configured such that the housing 502 of the surgical tool 500 is rotated counter-clockwise rather than clockwise. Geometries other than a wedge may be employed, such as an arch-shaped ramp, given that the structure is able to depress the pusher plate when rotating.

The pusher plate 704 is an actuator that disengages the plurality of couplers 512 from the surgical tool 500. Similar to the plurality of torque couplers 314, each of the couplers 512 may be coupled to one or more springs that bias each coupler 512 to spring outwards away from the sterile adapter 506. The plurality of couplers 512 are further configured to translate in an axial direction, i.e., protract away from and retract into the sterile adapter 506. The pusher plate 704 actuates the translational movement of the couplers 512. As the pusher plate 704 is depressed by the wedge 702, the pusher plate 704 causes the spring or plurality of springs coupled to each coupler 512 to compress, resulting in the couplers 512 retracting into the sterile adapter 506. In the embodiment of FIG. 7, the pusher plate 704 is configured to cause simultaneous retraction of the plurality of couplers 512. Alternate embodiments may retract the couplers 512 in a specific sequence or a random order. In the embodiment of FIG. 7, the pusher plate 704 causes the plurality of couplers 512 to partially retract into the sterile adapter 506. This configuration allows a surgical tool 500 to be de-articulated from the sterile adapter 506 before the surgical tool 500 is removed. This configuration also allows a user to de-articulate the surgical tool 500 from the sterile adapter 506 at any desired time without removing the surgical tool 500. Alternate embodiments may fully retract the plurality of couplers 512 into the sterile adapter 506 such that the effective height of each coupler 512 measured is zero. In some embodiments, the pusher plate 704 may cause the plurality of torque couplers 314 to retract synchronously with the plurality of respective couplers 512.

FIGS. 8A and 8B illustrate a process of engaging and disengaging a surgical tool from a sterile adapter, according to one embodiment. FIG. 8A illustrates a sterile adapter 506 and a surgical tool 500 in a secured position, such that the two components are secured together and the plurality of couplers 512 are fully engaged with respective instrument inputs 600 of the surgical tool 500. To achieve the secured position as illustrated in FIG. 8A, the elongated body 504 (not shown) of the surgical tool 500 is passed through the central hole 508 (not shown) of the sterile adapter 506 until mating surfaces of the surgical tool 500 and the sterile adapter 506 are in contact, and the surgical tool 500 and the sterile adapter 506 are secured to each other by a latching mechanism. In the embodiments of FIGS. 8A and 8B, the latching mechanism comprises a ledge 802 and a latch 804.

The ledge 802 is a structural component that secures the latch 804 in the secured position. In the embodiment of FIG. 8A, the ledge 802 is located within the housing 502 of the surgical tool 500 along the outer perimeter of the housing 502. As illustrated in FIG. 8A, the ledge 802 is oriented such that it rests below a protrusion on the latch 804, preventing the latch 804 and thereby the sterile adapter 506 from pulling away from the surgical tool 500 due to the sprung-up nature of the plurality of couplers 512, as described with regards to FIG. 7.

The latch 804 is a structural component that mates with the ledge 802 in the secured position. In the embodiment of FIG. 8A, the latch 804 protrudes from the mating surface of the sterile adapter 506. The latch 804 comprises a protrusion that is configured to rest against the ledge 802 when the surgical tool 500 is secured to sterile adapter 506. In the embodiment of FIG. 8A, the housing 502 of the surgical tool 500 is capable of rotating independent of the rest of the surgical tool 500. This configuration allows the housing 502 to rotate relative to the sterile adapter 506 such that the ledge 802 is secured against the latch 804, thereby securing the surgical tool 500 to the sterile adapter 502. In the embodiment of FIG. 8A, the housing 502 is rotated counter-clockwise to achieve the secured position, but other embodiments may be configured for clockwise rotation. In alternate embodiments, the ledge 802 and the latch 804 may have various geometries that lock the sterile adapter 506 and the surgical tool 500 in the secured position.

FIG. 8B illustrates the sterile adapter 506 and the surgical tool 500 in an unsecured position, in which the surgical tool 500 may be removed from the sterile adapter 506. As previously described, the housing 502 of the surgical tool 500 is capable of rotating independent of the rest of the surgical tool 500. This configuration allows the housing 502 to rotate even while the plurality of couplers 512 are engaged with the instrument inputs 600 of the surgical tool 500. To transition from the secured position to the unsecured position, a user rotates the housing 502 of the surgical tool 500 clockwise relative to the sterile adapter 506. During this rotation, the wedge 702 contacts the pusher plate 704 and progressively depresses the pusher plate 704 as it slides against the angled plane of the wedge 702, thereby causing the plurality of couplers 512 to retract into the sterile adapter 506 and disengage from the plurality of instrument inputs 600. Further rotation causes the latch 804 to contact an axial cam 806, which is structured similar to wedge 702. As the latch 804 contacts the axial cam 806 during rotation, the axial cam 806 causes the latch 804 to flex outwards away from the surgical tool 500 such that the latch 804 is displaced from the ledge 802. In this unsecured position, the plurality of couplers 512 are retracted, and the surgical tool 500 can be removed from the sterile adapter 506, in the embodiment of FIG. 8B. In other embodiments, the axial cam 806 may have various geometries such that rotation causes the latch 804 to flex outwards.

In alternate embodiments, the direction of rotation of the housing 502 of the surgical tool 500 may be configured as counter-clockwise rotation to unsecure the latch 804 from the ledge 802. Additionally, alternate embodiments may include similar components but the location of the components may be switched between the sterile adapter 506 and the surgical tool 500. For example, the ledge 802 may be located on the sterile adapter 506 while the latch 804 may be located on the surgical tool 500. In other embodiments, an outer portion of the sterile adapter 506 may be rotatable relative to the plurality of couplers 512 rather than the housing 502 of the surgical tool 500. Alternate embodiments may also include a feature to lock the rotation of the housing 502 of the surgical tool 502 when the housing 502 is fully rotated relative to the instrument inputs 600. This configuration prevents rotation of the surgical tool if the instrument inputs 600 have been de-articulated from the couplers 512. In some embodiments, the retraction and protraction of the couplers 512 may be coupled with a respective retraction and protraction of the torque couplers 314, such that a coupler 512 engaged with a torque coupler 314 will translate together.

Figure 9B:
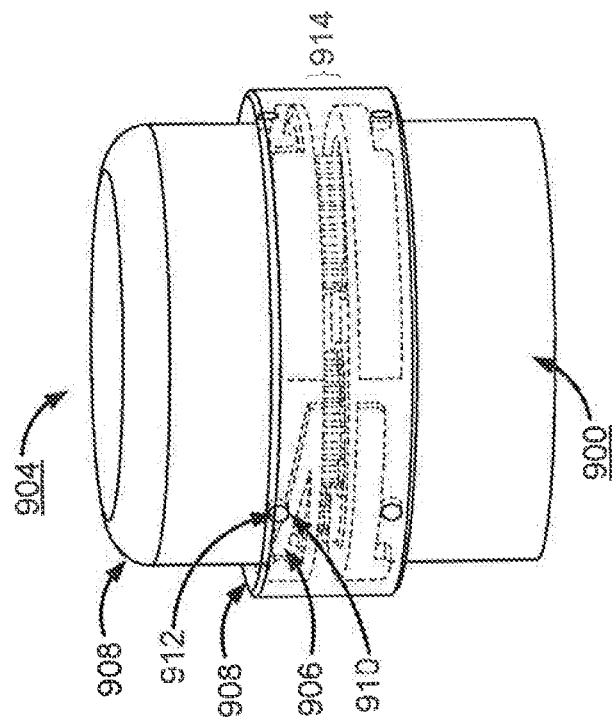
FIGS. 9A and 9B illustrate a process of engaging and disengaging a surgical tool from a sterile adapter, according to an additional embodiment.
Figure 9A:
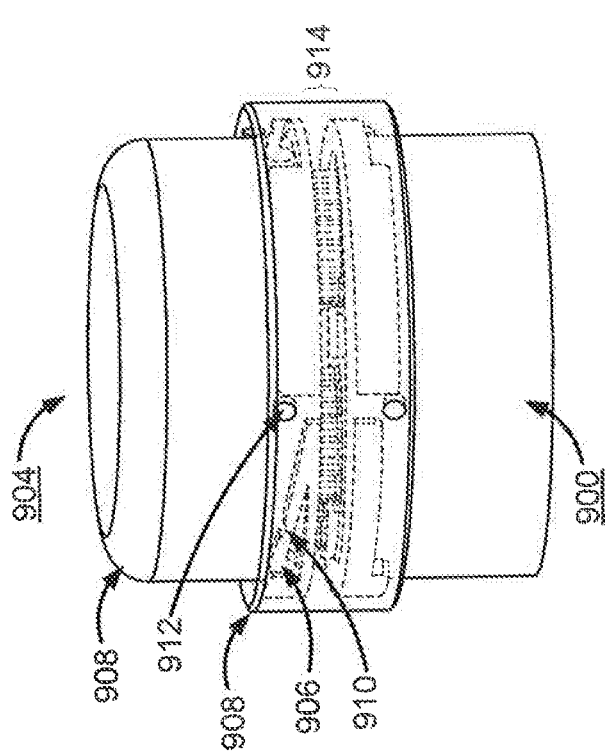

FIGS. 9A and 9B illustrate a process of surgical tool engagement and disengagement of a surgical tool from a sterile adapter, according to another embodiment. In the embodiment of FIGS. 9A and 9B, a sterile adapter 900 may include an outer band 902 that secures the surgical tool 904 to the sterile adapter 900. As illustrated in FIGS. 9A and 9B, the surgical tool 902 comprises a ramp 906 on the outer surface of the housing 908. The ramp 906 includes a notch 910 that is configured to receive a circular protrusion 912, which is positioned on an inner surface of the outer band 902 of the sterile adapter 900. The outer band 902 is capable of rotating independent of and relative to the sterile adapter 900 and the surgical tool 904. As the outer band 902 rotates in a first direction, the circular protrusion 912 glides up the surface of the ramp 906 until the circular protrusion 912 is nested within the notch 910, thereby securing the sterile adapter 900 and the surgical tool 904 together. Rotation of the outer band 902 in a second direction causes the sterile adapter 900 and the surgical tool 904 to unsecure from each other. In certain embodiments, this mechanism may be coupled with a de-articulation of the plurality of couplers 914 on the sterile adapter 900, as described with regards to FIGS. 7-8.

Alternative embodiments of surgical tool disengagement may include additional features, such as an impedance mode. With an impedance mode, the surgical robotics system may control whether the surgical tool can be removed from the sterile adapter by a user. The user may initiate the disengagement mechanism by rotating the outer housing of the surgical tool and unsecuring the surgical tool from the sterile adapter, but the surgical robotics system may not release the couplers from the instrument inputs. Only once the surgical robotics system has transitioned into the impedance mode are the couplers released and the user can remove the surgical tool. An advantage of keeping the surgical tool engaged is that the surgical robotics system can control the end-effectors of the surgical tool and position them for tool removal before the surgical tool is removed to minimize damage to the surgical tool. To activate an impedance mode, the pusher plate 704 may have a hard-stop such that the pusher plate can be depressed up to a certain distance. In some embodiments, the hard-stop of the pusher plate may be adjustable such that the hard-stop coincides with the maximum amount of rotation of the housing of the surgical tool. Thus, once the full rotation is reached, the hard-stop is also met by the pusher plate. A plurality of sensors may detect these events and trigger the impedance mode.

Certain situations may require emergency tool removal during a surgical procedure in which the impedance mode may not be desirable. In some embodiments, the hard-stop of the pusher plate may have compliance, such that the hard-stop may yield in an emergency. The hard-stop of the pusher plate may be coupled to a spring, allowing the hard-stop to yield in response to additional force. In other embodiments, the hard-stop of the pusher plate may be rigid such that emergency tool removal occurs by removing the latch that secures the surgical tool to the sterile adapter.

V. Roll Mechanism

Figure 10A:
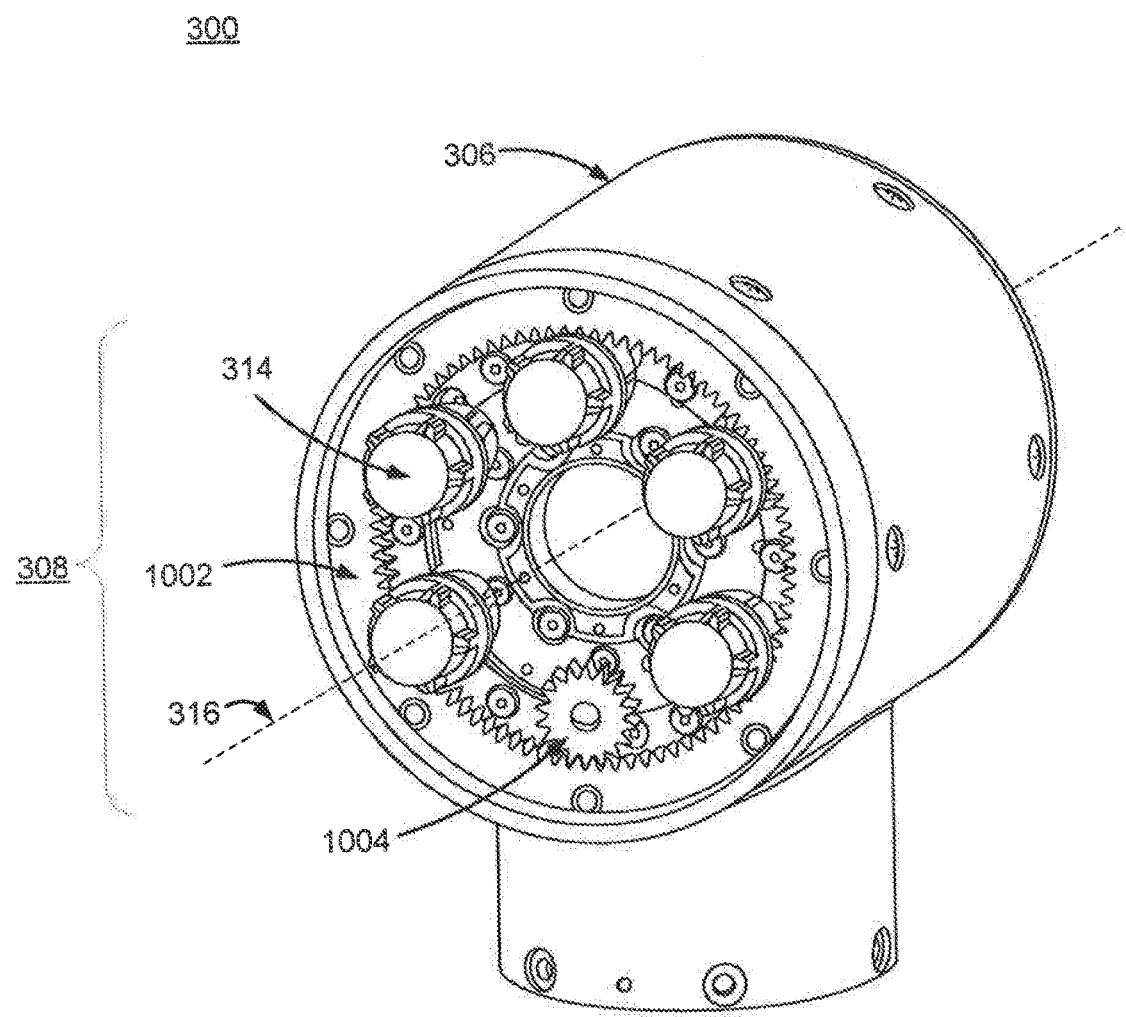
FIG. 10A illustrates a perspective view of a mechanism for rolling a surgical tool holder within an instrument device manipulator, according to one embodiment.

FIG. 10A illustrates a perspective view of a mechanism for rolling a surgical tool holder 308 within an instrument device manipulator 300, according to one embodiment. As illustrated in FIG. 10A, the attachment interface 310 is removed to expose the roll mechanism. This mechanism allows the surgical tool holder 308 to continuously rotate or "roll" about the rotational axis 316 in either direction. The roll mechanism comprises a stator gear 1002 and a rotor gear 1004.

The stator gear 1002 is a stationary gear configured to mate with the rotor gear 1004. In the embodiment of FIG. 10A, the stator gear 1002 is a ring-shaped gear comprising gear teeth along the inner circumference of the ring. The stator gear 1002 is fixedly attached to the outer housing 306 behind the attachment interface 310. The stator gear 1002 has the same pitch as the rotor gear 1004, such that the gear teeth of the stator gear 1002 are configured to mate with the gear teeth of the rotor gear 1004. The stator gear 1002 may be composed of rigid materials (e.g., metals or hard plastics).

The rotor gear 1004 is a rotating gear configured to induce rotation of the surgical tool holder 308. As illustrated in FIG. 10A, the rotor gear 1004 is a circular gear comprising gear teeth along its outer circumference. The rotor gear 1004 is positioned behind the attachment interface 310 and within the inner circumference of the stator gear 1002 such that the gear teeth of the rotor gear 1004 mate with the gear teeth of the stator gear. As previously described, the rotor gear 1004 and the stator gear 1002 have the same pitch. In the embodiment of FIG. 10A, the rotor gear 1004 is coupled to a drive mechanism (e.g., a motor) that causes the rotor gear 1004 to rotate in a clockwise or counter-clockwise direction. The drive mechanism may receive signals from an integrated controller within the surgical tool holder assembly 304. As the drive mechanism causes the rotor gear 1004 to rotate, the rotor gear 1004 travels along the gear teeth of the stator gear 1002, thereby causing the surgical tool holder 308 to rotate. In this configuration, the rotor gear 1004 is capable of continuously rotating in either direction and thus allows the surgical tool holder 308 to achieve infinite roll about the rotational axis 316. Alternate embodiments may use similar mechanisms to allow for infinite roll, such as a configuration of a ring gear and a pinion gear.

Figure 10B:
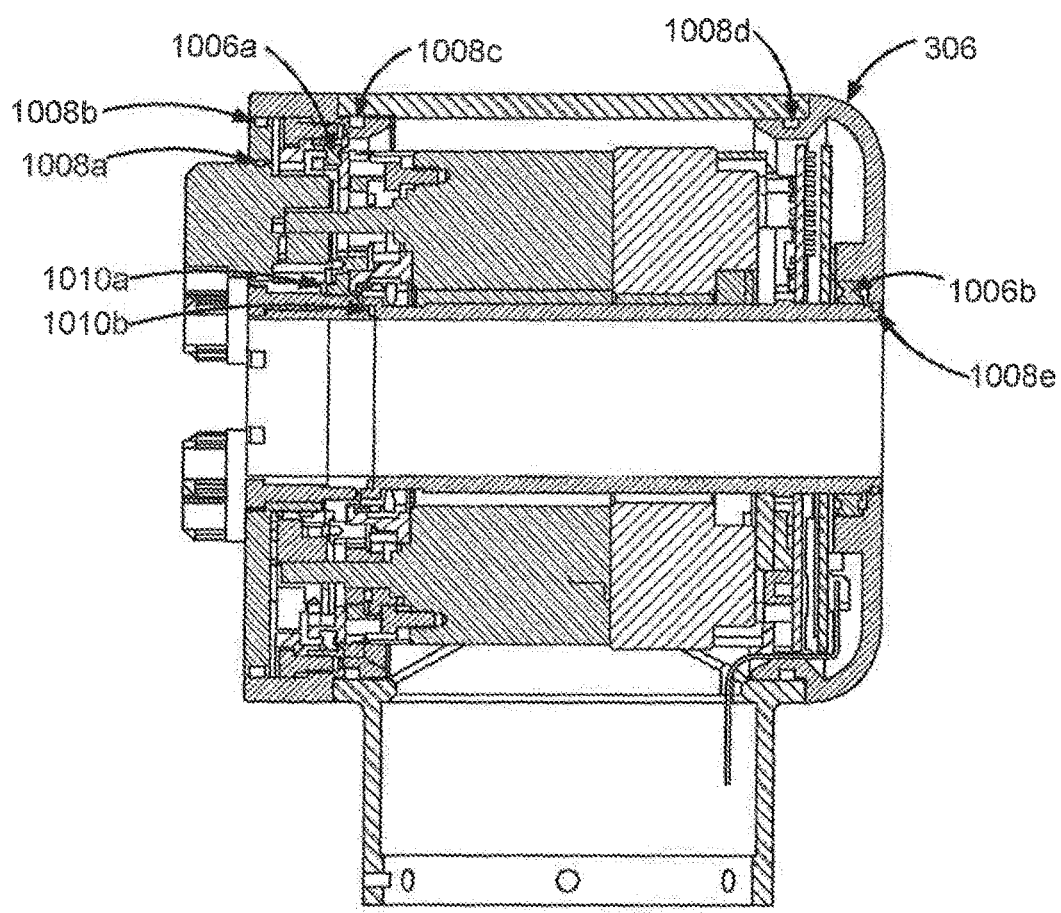
FIG. 10B illustrates a cross-sectional view of an instrument device manipulator, according to one embodiment.

FIG. 10B illustrates a cross-sectional view of an instrument device manipulator 300, according to one embodiment. As illustrated in FIB. 10B, the roll mechanism is coupled with a plurality of bearing 1006. A bearing is a mechanical component that reduces friction between moving parts and facilitates rotation around a fixed axis. One bearing alone can support the radial or torsional loading as the surgical tool holder 308 rotates within the outer housing 306. In the embodiment of FIG. 10B, the IDM 300 includes two bearings 1006a, 1006b fixedly attached to the surgical tool holder 308 such that a plurality of components (such as balls or cylinders) within the bearings 1006 contacts the outer housing 306. A first bearing 1006a is secured at a first end behind the attachment interface 310 and a second bearing 1006b is secured at a second end. This configuration improves rigidity and support between the first end and the second end of the surgical tool holder 308 as the surgical tool holder 308 rotates within the outer housing 306. Alternate embodiments may include additional bearings that provide additional support along the length of the surgical tool holder.

FIG. 10B also illustrates sealing components within the IDM 300, according to one embodiment. The IDM 300 comprises a plurality of O-rings 1008 and a plurality of gaskets 1010 which are configured to seal a junction between two surfaces to prevent fluids from entering the junction. In the embodiment of FIG. 10B, the IDM includes O-rings 1008a, 1008b, 1008c, 1008d, 1008e between junctions of the outer housing and gaskets 1010a, 1010b between junctions within the surgical tool holder 308. This configuration helps to maintain sterility of the components within the IDM 300 during a surgical procedure. Gaskets and O-rings are typically composed of strong elastomeric materials (e.g., rubber).

VI. Electrical Componentry

Figure 10C:
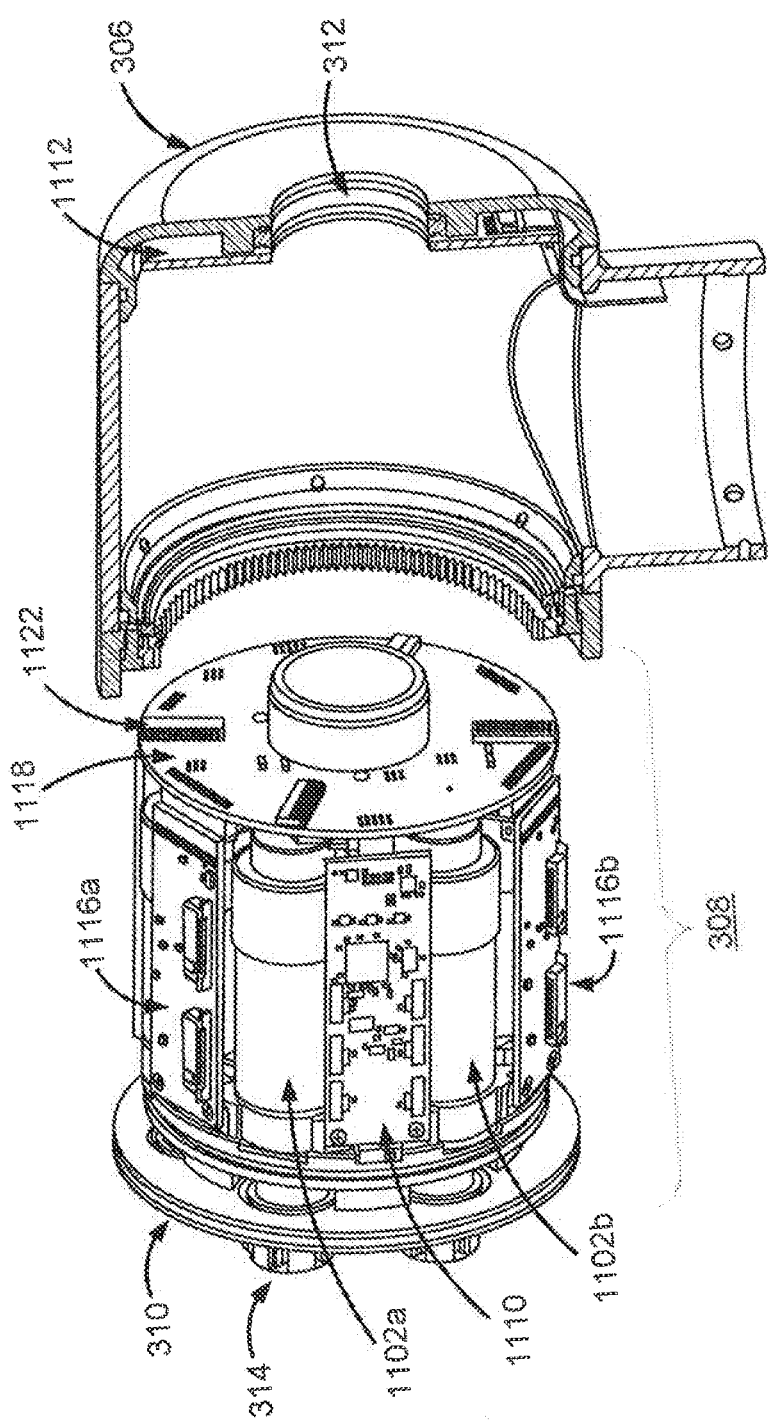
FIGS. 10C and 10D illustrates partially exploded, perspective views of the internal components of an instrument device manipulator and certain electrical components thereof, according to one embodiment.

FIG. 10C illustrates a partially exploded, perspective view of the internal components of an instrument device manipulator and certain electrical components thereof, according to one embodiment. The internal components of the surgical tool holder 308 include a plurality of actuators 1102, a motor, a gearhead (not shown), a torque sensor (not shown), a torque sensor amplifier 1110, a slip ring 1112, a plurality of encoder boards 1114, a plurality of motor power boards 1116, and an integrated controller 1118.

The plurality of actuators 1102 drive the rotation of each of the plurality of torque couplers 314. In the embodiment of FIG. 10C, an actuator, such as 1102a or 1102b, is coupled to a torque coupler 314 via a motor shaft. The motor shaft may be a keyed shaft such that it includes a plurality of grooves to allow the motor shaft to securely mate to a torque coupler 314. The actuator 1102 causes the motor shaft to rotate in a clockwise or counter-clockwise direction, thereby causing the respective torque coupler 314 to rotate in that direction. In some embodiments, the motor shaft may be torsionally rigid but spring compliant, allowing the motor shaft and thus the torque coupler 314 to rotate and to translate in an axial direction. This configuration may allow the plurality of torque couplers 314 to retract and protract within the surgical tool holder 308. Each actuator 1102 may receive electrical signals from the integrated controller 1118 indicating the direction and amount to rotate the motor shaft. In the embodiment of FIG. 10C, the surgical tool holder 308 includes five torque couplers 314 and thus five actuators 1102.

The motor drives the rotation of the surgical tool holder 308 within the outer housing 306. The motor may be structurally equivalent to one of the actuators, except that it is coupled to the rotor gear 1004 and stator gear 1002 (see FIG. 10A) for rotating the surgical tool holder 308 relative to the outer housing 306. The motor causes the rotor gear 1004 to rotate in a clockwise or counter-clockwise direction, thereby causing the rotor gear 1004 to travel about the gear teeth of the stator gear 1002. This configuration allows the surgical tool holder 308 to continuously roll or rotate without being hindered by potential wind-up of cables or pull-wires. The motor may receive electrical signals from the integrated controller 1118 indicating the direction and amount to rotate the motor shaft.

The gearhead controls the amount of torque delivered to the surgical tool 500. For example, the gearhead may increase the amount of torque delivered to the instrument inputs 600 of the surgical tool 500. Alternate embodiments may be configured such that the gearhead decreases the amount of torque delivered to the instrument inputs 600.

The torque sensor measures the amount of torque produced on the rotating surgical tool holder 308. In the embodiment shown in FIG. 10C, the torque sensor is capable of measuring torque in the clockwise and the counter-clockwise direction. The torque measurements may be used to maintain a specific amount of tension in a plurality of pull-wires of a surgical tool. For instance, some embodiments of the surgical robotics system may have an auto-tensioning feature, wherein, upon powering on the surgical robotics system or engaging a surgical tool with an IDM, the tension on the pull-wires of the surgical tool will be pre-loaded. The amount of tension on each pull-wire may reach a threshold amount such that the pull-wires are tensioned just enough to be taut. The torque sensor amplifier 1110 comprises circuitry for amplifying the signal that measures the amount of torque produced on the rotating surgical tool holder 308. In some embodiments, the torque sensor is mounted to the motor.

The slip ring 1112 enables the transfer of electrical power and signals from a stationary structure to a rotating structure. In the embodiment of FIG. 10C, the slip ring 1112 is structured as a ring including a central hole that is configured to align with the passage 312 of the surgical tool holder 308, as is also shown in an additional perspective view of the slip ring 1112 in FIG. 10D. A first side of the slip ring 1112 includes a plurality of concentric grooves 1120 while a second side of the slip ring 1112 includes a plurality of electrical components for the electrical connections provided from the surgical arm and the base 302, as described with regards to FIG. 3. The slip ring 1112 is secured to the outer housing 306 of the surgical tool holder 308 at a specific distance from the outer housing 306 to allocate space for these electrical connections. The plurality of concentric grooves 1120 are configured to mate with a plurality of brushes 1122 attached to the integrated controller. The contact between the grooves 1120 and the brushes 1122 enables the transfer of electrical power and signals from the surgical arm and base to the surgical tool holder.

The plurality of encoder boards 1114 read and process the signals received through the slip ring from the surgical robotic system. Signals received from the surgical robotic system may include signals indicating the amount and direction of rotation of the surgical tool, signals indicating the amount and direction of rotation of the surgical tool's end-effectors and/or wrist, signals operating a light source on the surgical tool, signals operating a video or imaging device on the surgical tool, and other signals operating various functionalities of the surgical tool. The configuration of the encoder boards 1114 allows the entire signal processing to be performed completely in the surgical tool holder 308. The plurality of motor power boards 1116 each comprises circuitry for providing power to the motors.

The integrated controller 1118 is the computing device within the surgical tool holder 308. In the embodiment of FIG. 10C, the integrated controller 1118 is structured as a ring including a central hole that is configured to align with the passage 312 of the surgical tool holder 308. The integrated controller 1118 includes a plurality of brushes 1122 on a first side of the integrated controller 1118. The brushes 1122 contact the slip ring 1112 and receive signals that are delivered from the surgical robotics system through the surgical arm, the base 302, and finally through the slip ring 1112 to the integrated controller 1118. As a result of the received signals, the integrated controller 1118 is configured to send various signals to respective components within the surgical tool holder 308. In some embodiments, the functions of the encoder boards 1114 and the integrated controller 1118 may be distributed in a different manner than is described here, such that the encoder boards 1114 and the integrated controller 1118 may perform the same functions or some combination thereof.

Figure 10D:
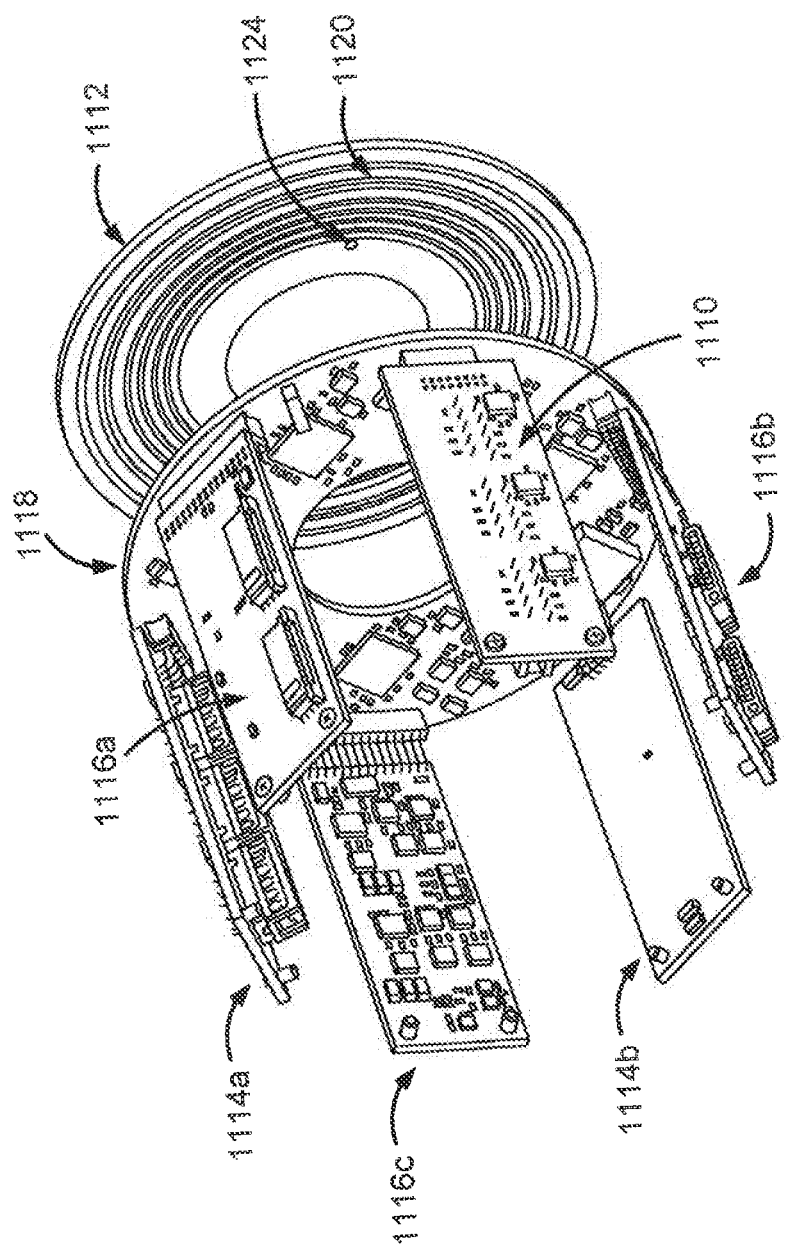

FIG. 10D illustrates a partially exploded, perspective view of the internal components of an instrument device manipulator and certain electrical components thereof, according to one embodiment. The embodiment of FIG. 10D includes two encoder boards 1114a and 1114b, a torque sensor amplifier 1110, and three motor power boards 1116a, 1116b, and 1116c. These components are secured to the integrated controller 1118 and protrude outwards, extending perpendicularly from the integrated controller 1118. This configuration provides room for the plurality of actuators 1102 and motor to be positioned within the electrical boards.

As discussed with regards to FIG. 10C, the slip ring 1112 is secured at a specific distance from the outer housing 306. To ensure correct space allocation between the slip ring 1112 and the outer housing 306 for the electrical connections from the surgical arm and base 302 to the slip ring 1112, in the embodiment of FIG. 10D, the slip ring 1112 is supported by a plurality of alignment pins, a plurality of coil springs, and a shim. The slip ring 1112 includes a hole 1124 on each side of the center hole of the slip ring 1112 that is configured to accept a first side of an alignment pin while a second side of the alignment pin is inserted into a respective hole in the outer housing 306. The alignment pins may be composed of rigid materials (e.g., metal or hard plastics). The plurality of coil springs is secured around the center of the slip ring 1112 and configured to bridge the space and maintain contact between the slip ring 1112 and the outer housing 306. The coil springs may beneficially absorb any impact to the IDM 300. The shim is ring-shaped spacer that is positioned around the center hole of the slip ring 1112 to add further support between the slip ring 1112 and the outer housing 306. In addition, these components provide stability to the slip ring 1112 as the plurality of brushes 1122 on the integrated controller 1118 contact and rotate against the plurality of concentric grooves 1120. In alternate embodiments, the number of alignment pins, coil springs, and shims may vary until the desired support between the slip ring 1112 and the outer housing 306 is achieved.

Figure 10E:
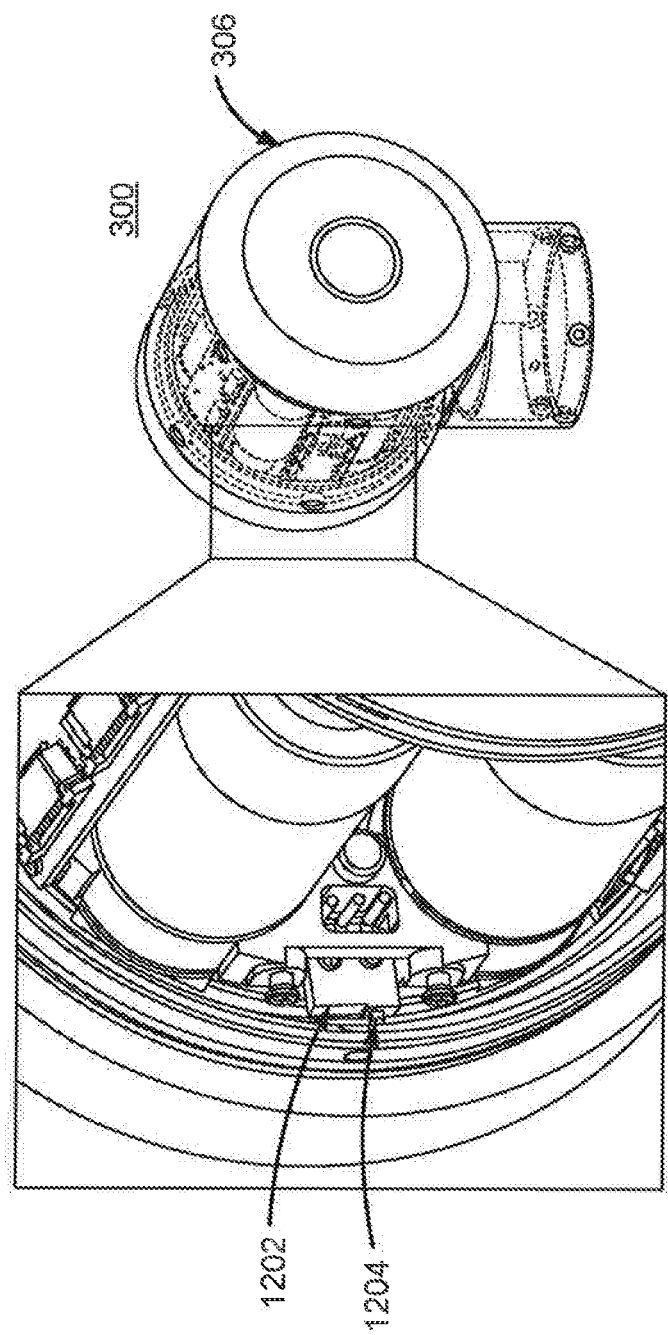
FIG. 10E illustrates a zoomed-in, perspective view of electrical components of an instrument device manipulator for roll indexing the surgical tool holder, according to one embodiment.

FIG. 10E illustrates a zoomed-in, perspective view of electrical components of an instrument device manipulator 300 for roll indexing the surgical tool holder 308, according to one embodiment. Roll indexing monitors the position of the surgical tool holder 308 relative to the outer housing 306 such that the position and orientation of the surgical tool 500 is continuously known by the surgical robotics system. The embodiment of FIG. 10E includes a micro switch 1202 and a boss 1204. The micro switch 1202 and the boss 1204 are secured within the surgical tool holder 308. The boss 1204 is a structure on the outer housing 306 that is configured to contact the micro switch 1202 as the surgical tool holder 308 rotates, thus activating the micro switch each time there is contact with the boss 1204. In the embodiment of FIG. 10E, there is one boss 1204 that serves as a single reference point for the micro switch 1202.

VII. Instruments Having Instrument Based Insertion Architectures

Various tools or instruments can attach to the IDM 300, including instruments used for laparoscopic, endoscopic and endoluminal surgery. The instruments described herein are particularly novel, as they include instrument based insertion architectures that reduce the reliance on robotic arms for insertion. In other words, insertion of an instrument (e.g., towards a surgical site) can be facilitated by the design and architecture of the instrument. For example, in some embodiments, wherein an instrument comprises an elongated shaft and a handle, the architecture of the instrument enables the elongated shaft to translate relative to the handle along an axis of insertion.

The instruments described herein incorporate instrument based insertion architectures that alleviate many issues. Instruments that do not incorporate an instrument based insertion architecture rely on a robotic arm and its IDM for insertion. In this arrangement, to achieve instrument insertion, the IDM may need to be moved in and out, therefore requiring additional motor power and arm link size for moving the additional mass in a controlled manner. In addition, the larger volume creates a much larger swept volume that can result in collisions during operation. By incorporating instrument based insertion architectures, the instruments described herein typically have a reduced swung mass, as the instrument itself (e.g., its shaft) moves along an insertion axis with less reliance on the robotic arm.

Some embodiments of the instruments described herein may have novel instrument based insertion architectures that not only allow for insertion of the instrument, but also allow an end effector of the instrument to actuate without interference. For example, in some embodiments, an instrument comprises a first actuation mechanism for actuating an end effector and a second actuation mechanism for causing translation of a portion of the instrument (e.g., a shaft) along an axis of insertion. The first actuation mechanism is advantageously decoupled from the second actuation mechanism such that the actuation of the end effector is not affected by the insertion of the instrument, and vice versa.

Figure 11:
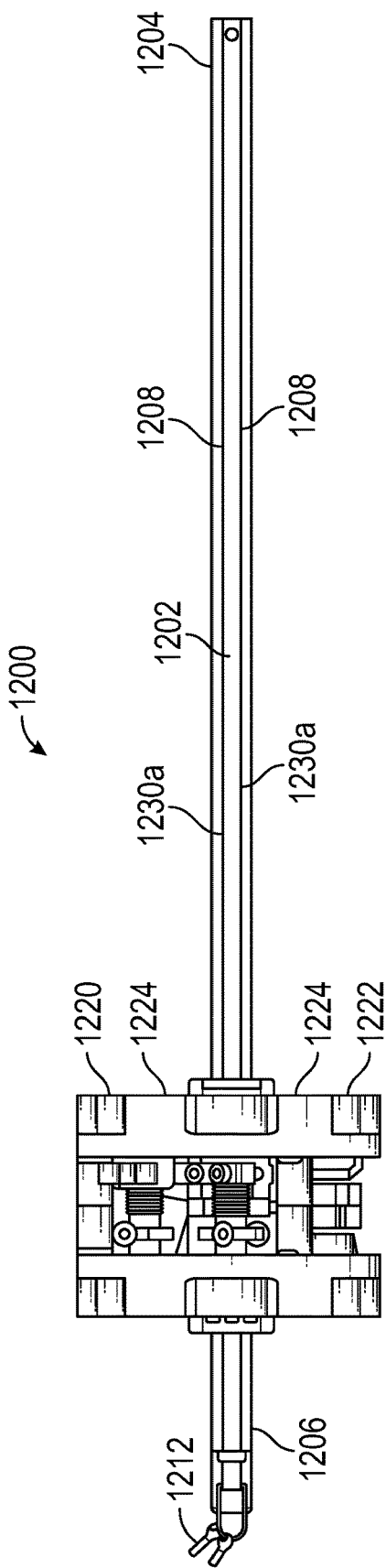
FIG. 11 illustrates a side view of an instrument having an instrument based insertion architecture, according to one embodiment.

FIG. 11 illustrates a side view of an instrument having an instrument based insertion architecture, according to one embodiment. The design and architecture of the instrument 1200 enables the instrument (e.g., its shaft) to translate along an insertion axis with less reliance on movement of a robotic arm for insertion.

The instrument 1200 comprises an elongated shaft 1202, an end effector 1212 connected to the shaft 1202, and a handle 1220 coupled to the shaft 1202. The elongated shaft 1202 comprises a tubular member having a proximal portion 1204 and a distal portion 1206. The elongated shaft 1202 comprises one or more channels or grooves 1208 along its outer surface. The grooves 1208, which are most visible in the cross-sectional view of the shaft 1202, are configured to receive one or more wires or cables 1230 therethrough. One or more cables 1230 thus run along an outer surface of the elongated shaft 1202. In other embodiments, cables 1230 can also run through the shaft 1202, as shown in the schematic drawing in FIG. 21. In some embodiments, cables 1230 that run through the shaft 1202 are not exposed. In some embodiments, manipulation of the one or more of these cables 1230 (e.g., via the IDM 300) results in actuation of the end effector 1212.

The end effector 1212 comprises one or more laparoscopic, endoscopic or endoluminal components designed to provide an effect to a surgical site. For example, the end effector 1212 can comprise a wrist, grasper, tines, forceps, scissors, or clamp. In the present embodiment shown in FIG. 11, one or more of the cables 1230 that extend along the grooves 1208 on the outer surface of the shaft 1202 actuate the end effector 1212. The one or more cables 1230 extend from a proximal portion 1204 of the shaft 1202, through the handle 1220 and toward a distal portion 1206 of the shaft 1202, where they actuate the end effector 1212.

The instrument handle 1220, which may also be referred to as an instrument base, may generally comprise an attachment interface 1222 having one or more mechanical inputs 1224, e.g., receptacles, pulleys or spools, that are designed to be reciprocally mated with one or more torque couplers 314 on an attachment interface 310 of the IDM 300 (shown in FIG. 3). The attachment interface 1222 is capable of attaching to an IDM 300 via front-mount, back-mount and/or top mount. When physically connected, latched, and/or coupled, the mated mechanical inputs 1224 of the instrument handle 1220 may share axes of rotation with the torque couplers 314 of the IDM 300, thereby allowing the transfer of torque from the IDM 300 to the instrument handle 1220. In some embodiments, the torque couplers 314 may comprise splines that are designed to mate with receptacles on the mechanical inputs. Cables 1230 that actuate the end effector 1212 engage the receptacles, pulleys or spools of the handle 1220, such that the transfer of torque from the IDM 300 to the instrument handle 1220 results in actuation of the end effector.

Figure 12:
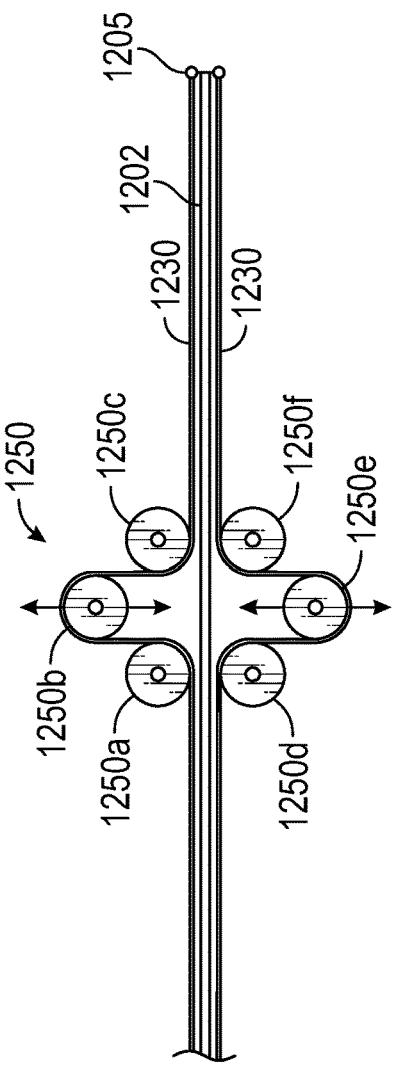
FIG. 12 illustrates a schematic diagram showing a first actuation mechanism for actuating an end effector, according to one embodiment.
Figure 16:
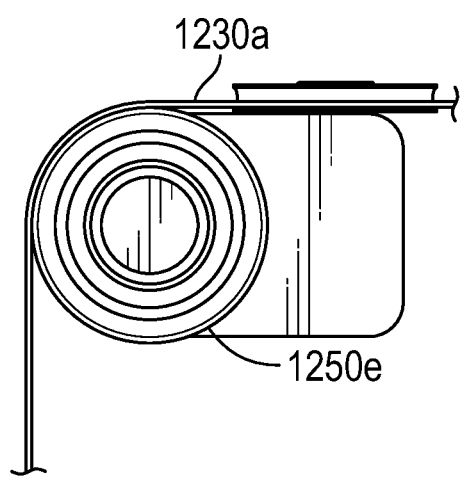
FIG. 16 illustrates a view of a pulley and cable of the instrument of FIG. 11, following actuation of the pulley, according to one embodiment.
Figure 17:
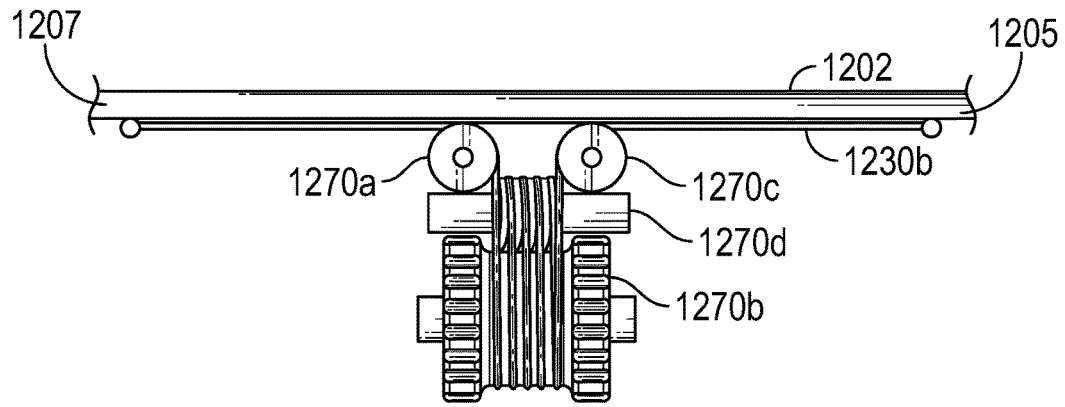
FIG. 17 illustrates a side view of a second actuation mechanism including a spool for shaft translation, according to one embodiment.

Some embodiments of the instrument 1200 comprise a first actuation mechanism that controls actuation of the end effector 1212. An embodiment of such a first actuation mechanism is schematically illustrated in FIG. 12. In addition, the instrument 1200 includes a second actuation mechanism that enables the shaft 1202 to translate relative to the handle 1220 along an axis of insertion. An embodiment of such a second actuation mechanism is shown in FIG. 17. Advantageously, the first actuation mechanism is decoupled from the second actuation mechanism, such that actuation of the end effector 1212 is not affected by the translation of the shaft 1202, and vice versa. Embodiments of the first and second actuation mechanisms that can be incorporated into a tool or instrument 1200 are described in more detail below with respect to FIGS. 12-20.

FIG. 12 illustrates a schematic diagram showing a first actuation mechanism for actuating an end effector, according to one embodiment. In some embodiments, the first actuation mechanism provides N+1 wrist motion, wherein N is the number of degrees of freedom provided by N+1 cables. The first actuation mechanism for actuating the end effector 1212 comprises at least one cable or cable segment 1230a that extends through at least one set of pulleys 1250. In the present embodiment, a first cable or cable segment 1230a extends through pulley members 1250a, 1250b, 1250c, while a second cable or cable segment 1230a extends through pulley members 1250d, 1250e, 1250f. The at least one cable 1230a is grounded at or near the proximal end 1205 of the shaft 1202, then extends through the at least one set of pulleys 1250 (which are located within the handle 1220), before terminating at the end effector 1212. Cable total path length is kept constant by grounding each cable 1230a at or near the proximal end 1205 of the shaft 1202, and relative length changes are made by moving pulleys (e.g., pulley members 1250b and 1250e) relative to each other (see arrows), thereby enabling actuation of the end effector 1212. In some embodiments, the pulleys can be moved via linear or rotary motion of corresponding mechanical inputs 1224. This first actuation mechanism advantageously permits free movement of the instrument shaft 1202 relative to the actuation pulleys 1250 (which will be accomplished by a second actuation mechanism described below), thereby allowing an additional cable to be included to permit insertion and retraction of the instrument shaft 1202 at the same time as end effector 1212 actuation.

Figure 13:
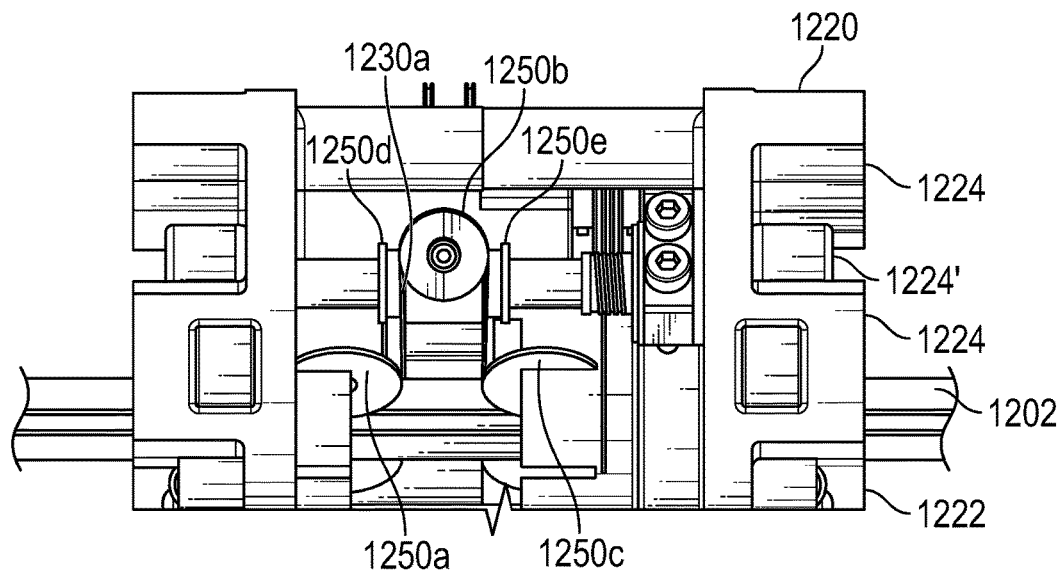
FIG. 13 illustrates a zoomed-in side view of a first actuation mechanism of the instrument of FIG. 11, according to one embodiment.
Figure 15:
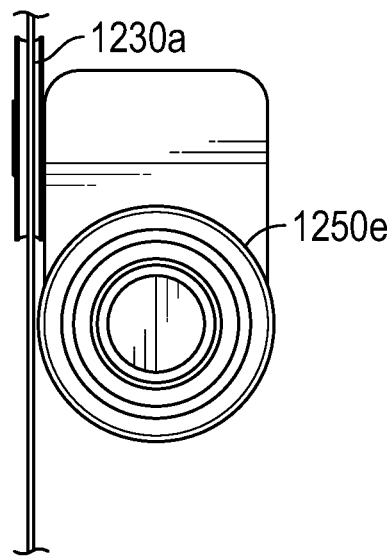
FIG. 15 illustrates a view of a pulley and cable of the instrument of FIG. 11, prior to actuation of the pulley, according to one embodiment.

FIG. 13 illustrates a zoomed-in side view of a first actuation mechanism of the instrument of FIG. 11, according to one embodiment. The first actuation mechanism corresponds with the schematic diagram shown in FIG. 12 and is designed to cause actuation of the end effector 1212, while permitting a separate second actuation mechanism to translate the shaft 1202 relative to the handle 1220. As shown in FIG. 13, the handle 1220 includes a set of bearings, spools, pulleys or pulley members 1250a, 1250b, 1250c, 1250d, 1250e (wherein pulleys 1250a, 1250b, 1250c correspond to the same set of pulleys in FIG. 12). A cable 1230a extends through the pulleys 1250a, 1250d, 1250b, 1250e, 1250c. Manipulation of a mechanical input (identified as 1224' in FIG. 13) causes rotary motion of the pulleys 1250d, 1250b, 1250e. The rotary motion of the pulleys 1250d, 1250b, 1250e changes the amount of cable 1230 that is received in the handle 1220, thereby actuating the end effector. The effect of the rotary motion of the pulleys on the cable 1230a is shown in FIGS. 15 and 16. Depending on the direction of the rotary motion, the pulleys 1250d, 1250e can either wound or "take up" cable 1230 in the handle 1220, or can unwound and "give out" cable 1230a in the handle 1220. Either way, the length of the cable 1230a changes within the handle 1220, thereby causing actuation of the end effector 1212. While the embodiment in FIG. 13 depicts a pulley system that is modified by rotary motion, in other embodiments, the pulley system can be modified by linear and/or rotary motion. In addition, one skilled in the art will appreciate that a change in length in the amount of cable 1230a in the handle 1220 can also change cable tension.

Figure 14:
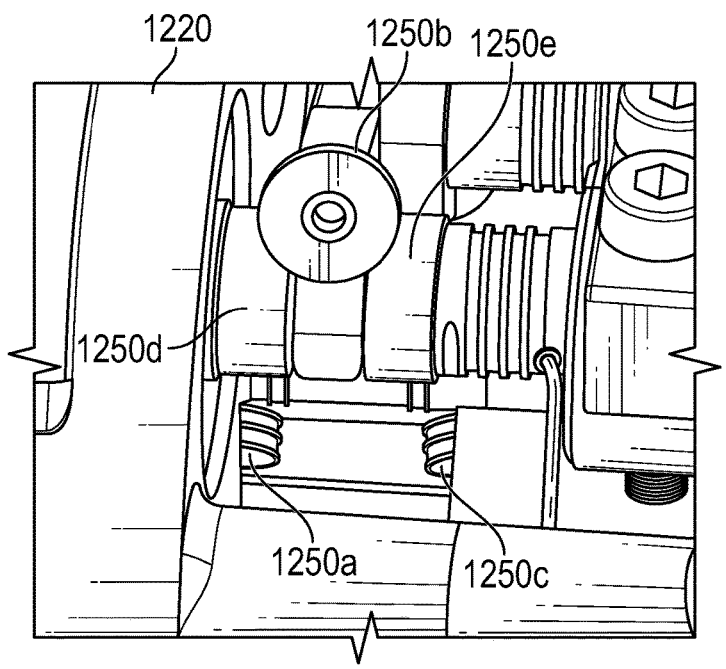
FIG. 14 illustrates a zoomed-in perspective view of a first actuation mechanism of the instrument of FIG. 11, according to one embodiment.

FIG. 14 illustrates a zoomed-in perspective view of a first actuation mechanism of the instrument of FIG. 11, according to one embodiment. From this view, one can see different details of the pulleys 1250a-e including the spools of the pulleys 1250a, 1250c.

FIGS. 15 and 16 illustrate a front view of a pulley member 1250e and cable of the instrument of FIG. 11, before and after actuation of the pulley member, according to one embodiment. Applying torque on the mechanical input 1224' rotates pulleys 1250e, 1250b and 1250d. As shown in FIG. 15, before actuation of the pulley 1250e, cable 1230a can run along one side of the pulley 1250e. As shown in FIG. 16, after actuation of the pulley 1250e, the cable 1230a is then wound and taken up by the pulley, thereby increasing the amount of cable 1230a within the handle 1220 to cause actuation of an end effector.

While embodiments in FIGS. 11-16 disclose one or more pulleys mounted on a rotary axis to change relative cable length, in other embodiments, mounting a pulley on a lever, gear or track based system to adjust location are additional options. In addition, ball spline rotary shafts that travel down a length of a tool could also be used to transmit forces in a mechanically remote way.

FIG. 17 illustrates a side view of a second actuation mechanism including a spool for shaft translation, according to one embodiment. The second actuation mechanism is designed to translate the shaft 1202 relative to the handle 1220 along an axis of insertion Like the first actuation mechanism that actuates the end effector 1212, the second actuation mechanism can also be incorporated within the handle 1220.

The second actuation mechanism comprises a cable or cable segment 1230*b* that engages a set of spools 1270*a*, 1270*b*, 1270*c*, 1270*d*. One end of the cable 1230*b* can be attached at or near a proximal end 1205 of the shaft 1202, while the other end of the cable 1230*b* can be attached at or near a distal end 1207 of the shaft 1202. The cable 1230*b* extends through the set of spools 1270*a*, 1270*b*, 1270*c*, of which spool 1270*b* is a capstan. Rotating a mechanical input of the handle 1220 causes rotation of the capstan, thereby driving cable 1230*b* in and out of the capstan. As cable 1230*b* is driven in and out of the capstan, this causes the shaft 1202 to translate relative to the handle 1220. Advantageously, by applying adequate pre-tension to the cable 1230*b* that is attached at both the proximal and distal end of the shaft 1202, frictional force can be used to drive the cable 1230*b* in and out, thereby moving the shaft 1202 relative to the handle 1220 without slipping.

Figure 18:
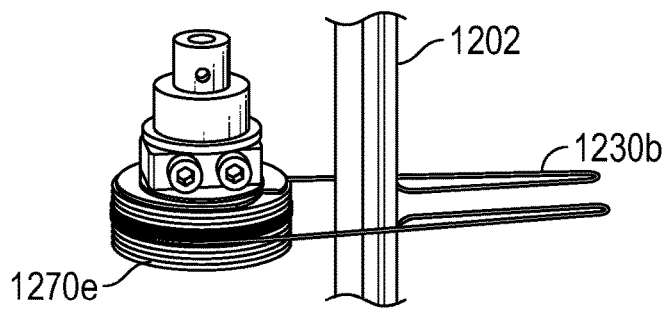
FIG. 18 illustrates a perspective view of an alternative spool using a single cable for shaft translation, according to one embodiment.
Figure 19:
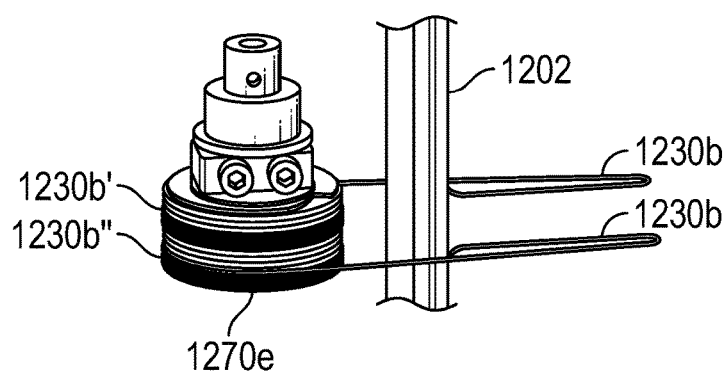
FIG. 19 illustrates a perspective view of an alternative spool using more than one cable for shaft translation, according to one embodiment.

In the present embodiment, the capstan 1270*b* comprises a zero-walk capstan. In other embodiments, such as shown in FIGS. 18 and 19, a capstan can be incorporated into the handle 1220 that can allow for cable walk. The zero-walk capstan architecture helps to manage multiple wraps of cable 1230*b* around the capstan 1270*b* without a helix angle on the groove to prevent the cable walk across the capstan 1270*b*, which could affect overall path length and change tension in the cable. By placing an additional pulley 1270*d* on an incline next to the capstan 1270*b*, a redirect to a parallel path on the capstan 1270*b* can be achieved, resulting in no walking action of the cable 1230*b* on the capstan 1270*b*.

FIGS. 18 and 19 present alternative embodiments to the zero-walk capstan shown in FIG. 17. In these embodiments, the capstan that drives shaft insertion is an enlarged capstan 1270*e* that can be incorporated into the architecture of the second actuation mechanism. With a large enough drive capstan 1270*e* and a small enough insertion stroke, the number of rotations of the capstan is small. For example, with a 22 mm drive capstan 1270*e* and a 350 mm insertion stroke, the number of rotations of the capstan 1270*e* for full insertion range is 5 rotations. If the distance that the cable goes to is large enough compared to the cable walk range of the capstan 1270*e*, the amount of fleet angle on the cable and path length change during insertion is small enough to be negligible. In some embodiments, the fleet angle can be between +/−2 degrees.

FIG. 18 illustrates a perspective view of an alternative spool using a single cable for shaft translation, according to one embodiment. The alternative spool comprises an enlarged capstan 1270*e* which is engaged by a single cable 1230*b*. In this embodiment, to actuate drive shaft insertion, the single cable 1230*b* has a large enough wrap angle to have enough capstan friction to drive. In some embodiments, the single cable 1230*b* is continuous and wraps around the capstan 1270*e* multiple times (e.g., 3, 4 or more times) to have a large enough wrap angle to drive the capstan and insertion.

FIG. 19 illustrates a perspective view of an alternative spool using more than one cable for shaft translation, according to one embodiment. The alternative spool comprises an enlarged capstan 1270*e* which is engaged by two separate segments 1230*b*', 1230*b*" of a single cable 1230*b*. Each of the segments 1230*b*', 1230*b*" terminates on the capstan 1270*e*. Unlike the embodiment in FIG. 18, the present embodiment does not rely on capstan friction to drive shaft insertion. In this embodiment, the cable 1230*b* is helixed to the outsides and then terminated to the spool at both the top and bottom. An advantage of the double termination approach shown in FIG. 19 is that it is resilient to loss of cable tension. As the double termination approach relies on a positive engagement rather than friction, slip cannot happen.

Figure 20:
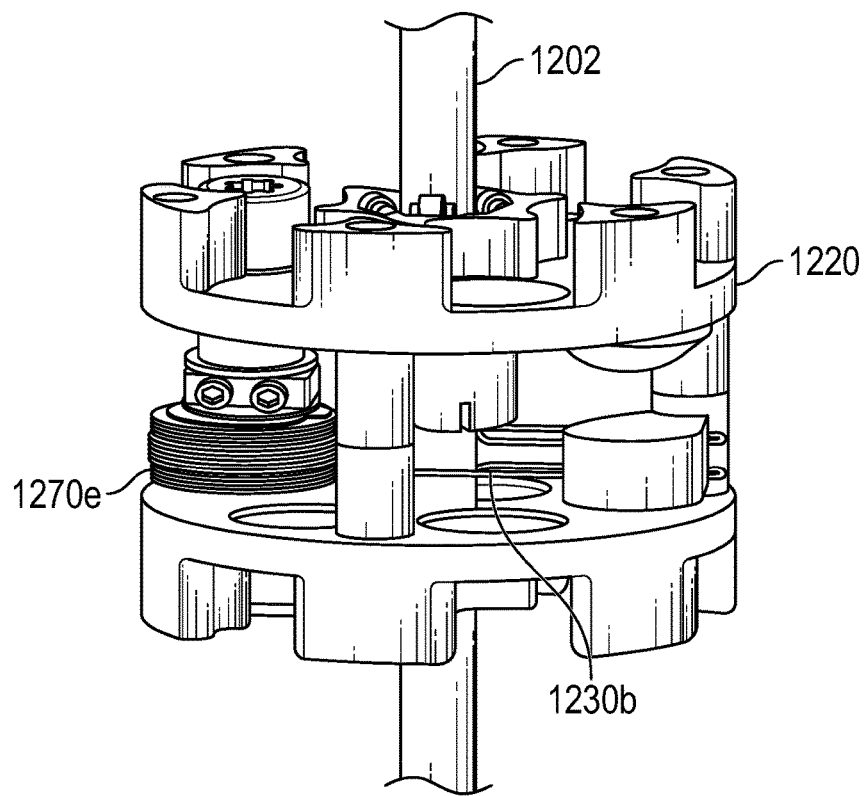
FIG. 20 illustrates a front view of a handle including the spool of FIG. 18, according to one embodiment.

FIG. 20 illustrates a front view of a handle including the spool of FIG. 18, according to one embodiment. From this view, one can see one possible position of the spool (e.g., the capstan 1270*e*) within the handle 1220. Advantageously, additional spools and pulleys can be provided within the handle 1220 to actuate the end effector 1212. For example, a pulley system for end effector actuation as represented in FIG. 12 can be incorporated into the handle in FIG. 20. Accordingly, the handle 1220 can incorporate multiple mechanisms for both end effector actuation and/or drive insertion. As shown in FIG. 20, the one or more pulleys guiding the cable 1230 onto the capstan 1270*e* are situated across the handle to increase cable distance. If the distance that the cable goes to is large enough compared to the cable walk range of the capstan 1270*e*, the amount of fleet angle on the cable and path length change during insertion is small enough to be negligible. In some embodiments, it is possible to have a traditional helix capstan and keep the length change and fleet angle to a minimum.

Figure 21:
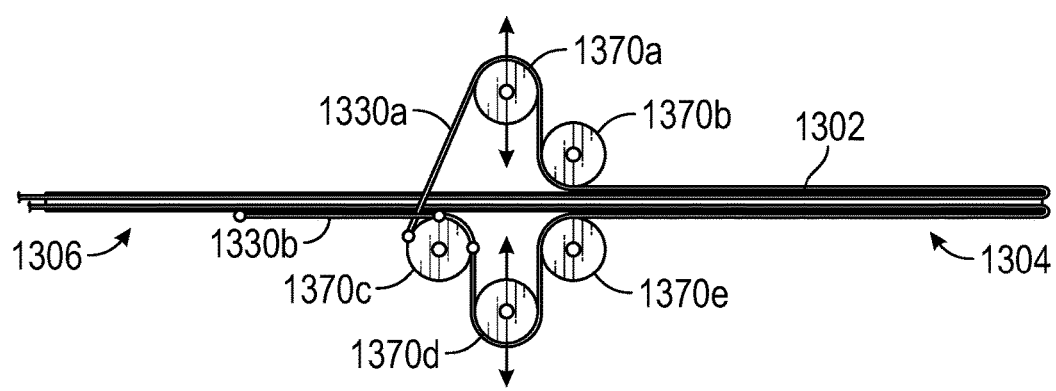
FIG. 21 illustrates a schematic diagram showing an alternative architecture for actuating an end effector and shaft translation, according to one embodiment.

FIG. 21 illustrates a schematic diagram showing an alternative architecture for actuating an end effector and shaft insertion, according to one embodiment. The architecture incorporates a first actuation mechanism for actuating an end effector and a second actuation mechanism for shaft insertion Like prior embodiments, the first actuation mechanism and the second actuation mechanism are decoupled, such that actuation of the end effector does not impact shaft insertion, and vice versa. However, in the present embodiment, the first actuation mechanism comprises one or more cables for actuating an end effector that terminate at an insertion spool (which is also used as part of the second actuation mechanism for shaft insertion), rather than terminating on the proximal and distal portions of the shaft as in the embodiment in FIG. 12. As a result of this architecture, during shaft insertion via a second actuation mechanism, one or more cables that are wound by the insertion spool are substantially counterbalanced by a length of one or more cables (used in a first actuation mechanism to actuate an end effector) that are unwound by the insertion spool. During end effector actuation via a first actuation mechanism, one is trading off the path lengths of the cables coming off of the insertion spool.

As shown in FIG. 21, the alternative architecture for end effector actuation and shaft insertion comprises a shaft 1302 having a proximal portion 1304 and a distal portion 1306 where an end effector is located. One or more spools 1370*a*, 1370*b*, 1370*c*, 1370*d*, 1370*e* (which are part of a handle) are positioned about the shaft 1302. Spool 1370*c* comprises an insertion spool. Rotation of the insertion spool 1370*c* in a first direction causes shaft translation relative to the handle in a first direction (e.g., in a direction of insertion), while rotation of the insertion spool 1370*c* in a second direction causes shaft translation relative to the handle in a second direction (e.g., in a direction of retraction). One or more cables or cable segments 1330*a* terminate to an end effector (e.g., a wrist) on one end and an insertion spool on the other. One or more additional cables or cable segments 1330*b* also begin at the insertion spool 1370*c* before terminating at, near or towards a distal portion 1306 of the shaft 1302.

In the present embodiment, a first actuation mechanism is provided wherein manipulation of one or more spools (e.g., spools 1370*a*, 1370*d*) via linear or rotary movement causes a change of length of the one or more cables 1330*a* within the handle. In some embodiments, the change of length of the one or more cables 1330*a* within the handle can include a change of the path length of one or more cables or cable segments within the handle. In this first actuation mechanism, the one or more cables 1330*a* can be considered "end effector" cables. Any change in length of the one or more cables 1330*a* in the handle that causes actuation of the end effector is counterbalanced by a length of the one or more cables 1330*b*.

In the present embodiment, a second actuation mechanism is provided wherein manipulation of the insertion spool 1370*c* via linear or rotary movement causes a change of length of the one or more cables 1330*b* within the handle. In this second actuation mechanism, the one or more cables 1330*b* can be considered "insertion" cables. Any change in length of the one or more cables 1330*b* in the handle that causes shaft insertion or retraction is counterbalanced by a length of the one or more cables 1330*a*. Under insertion and retraction, tension is maintained because equal amounts of the one or more end effector cables 1330*a* are being paid out as the one or more insertion cables 1330*b* are being taken up. The relative path length of the one or more end effector cables 1330*a* remains unchanged, so the end effector does not move under insertion.

Figure 22A:
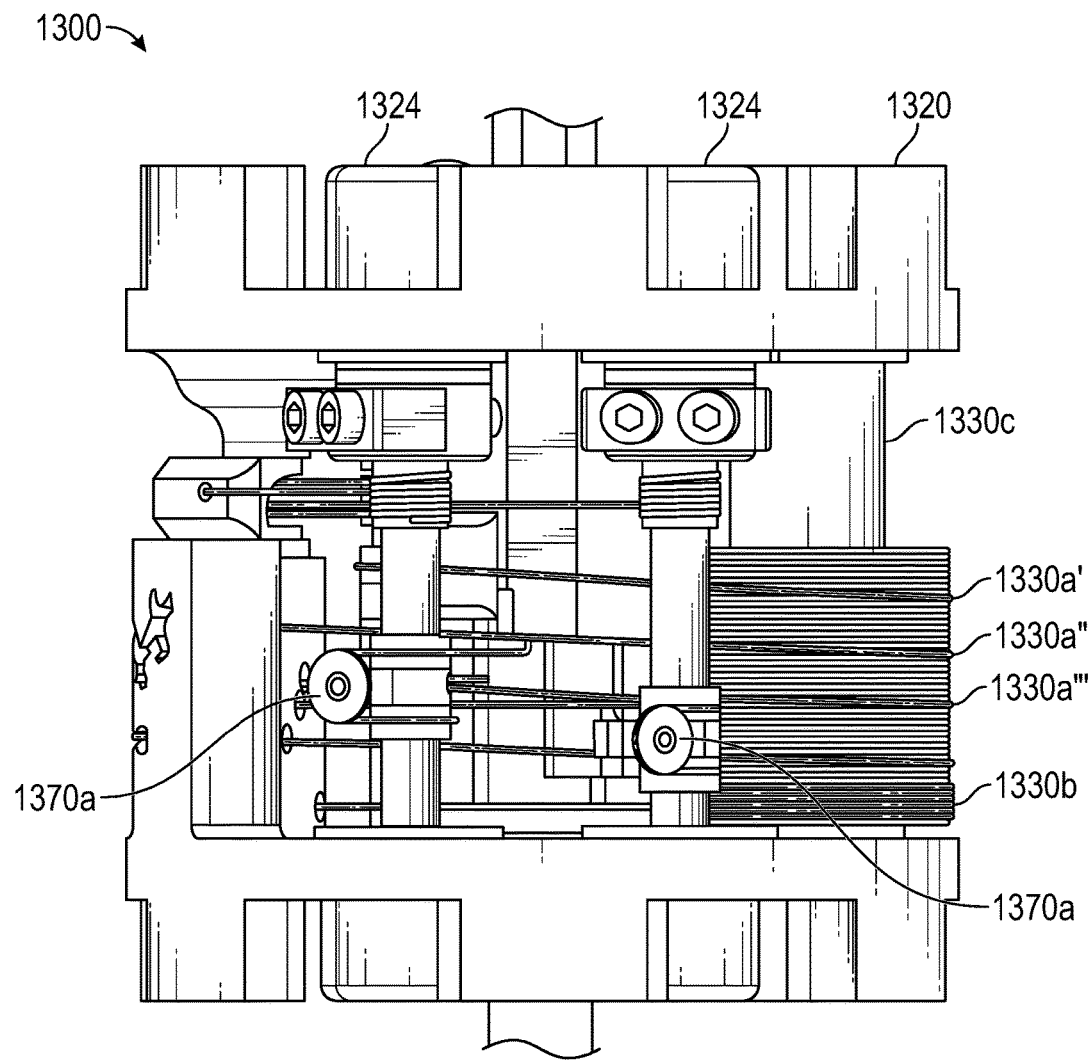
FIG. 22A illustrates a zoomed-in front view of an instrument incorporating the alternative architecture for actuating an end effector and shaft insertion of FIG. 21, according to one embodiment.
Figure 22B:
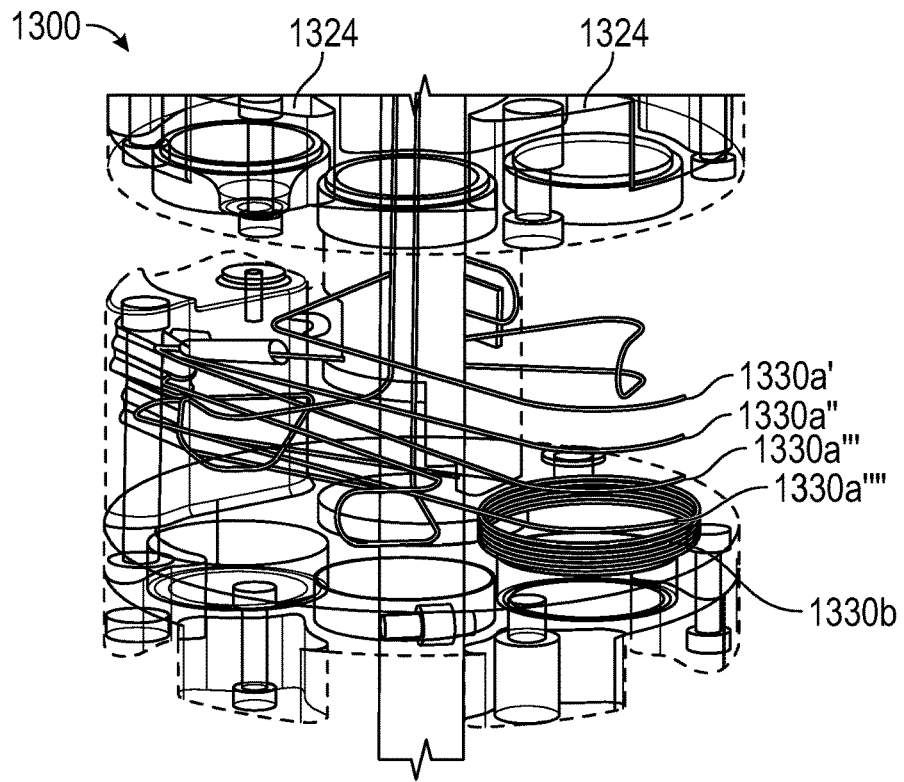
FIG. 22B illustrates a top perspective view of an instrument incorporating the alternative architecture for actuating an end effector and shaft insertion of FIG. 21, according to one embodiment.

FIG. 22A illustrates a zoomed-in front view of an instrument incorporating the alternative architecture for actuating an end effector and shaft insertion of FIG. 21, according to one embodiment. FIG. 22B illustrates a top perspective view of the instrument incorporating the alternative architecture for actuating an end effector and shaft insertion of FIG. 21. The instrument 1300 incorporates the first and second actuation mechanism shown in FIG. 21, and includes a handle 1320 comprising one or more mechanical inputs 1324, each corresponding to one or more spools 1370*a-e*, wherein at least one of the spools (1370*c*) comprises an insertion spool. One or more cables or cable segments 1330*a'*, 1330*a''*, 1330*a'''* and 1330*a''''*, each corresponding to a separate mechanical input 1324, terminate at the drive spool 1370*c*. Each of these cables 1330*a'*, 1330*a''*, 1330*a'''* and 1330*a''''* can engage with one or more spools akin to the one or more cables 1330*a* (shown in the schematic in FIG. 21). In a first actuation mechanism, these cables can serve as end effector cables, such that manipulation of their corresponding mechanical inputs 1324 causes a change of length of the cables within the handle. In some embodiments, the change of length of the one or more cables within the handle can include a change of the path length of one or more cables or cable segments within the handle. In some embodiments, a path length of the cables within the handle is changed. In some instances, the change of length in the one or more cables 1330*a'*, 1330*a''*, 1330*a'''*, 1330*a''''* within the handle 1320 that actuate the end effector is counterbalanced by a length of cable 1330*b*, which is akin to the similarly reference cable 1330*b* in FIG. 21. In other instances, under pure end effector actuation, the length of the cable 1330*b* in the handle is not changing. In a second actuation mechanism, the cable 1330*b* can serve as an insertion cable, such that manipulation of its corresponding mechanical input 1324 causes cable 1330*b* to be wound around the insertion spool 1370*c*. The amount of cable 1330*b* that is wound around the insertion spool 1370*c* that causes shaft insertion is counterbalanced by a length of the one or more cables 1330*a'*, 1330*a''*, 1330*a'''*, 1330*a''''* being unwound.

Figure 23:
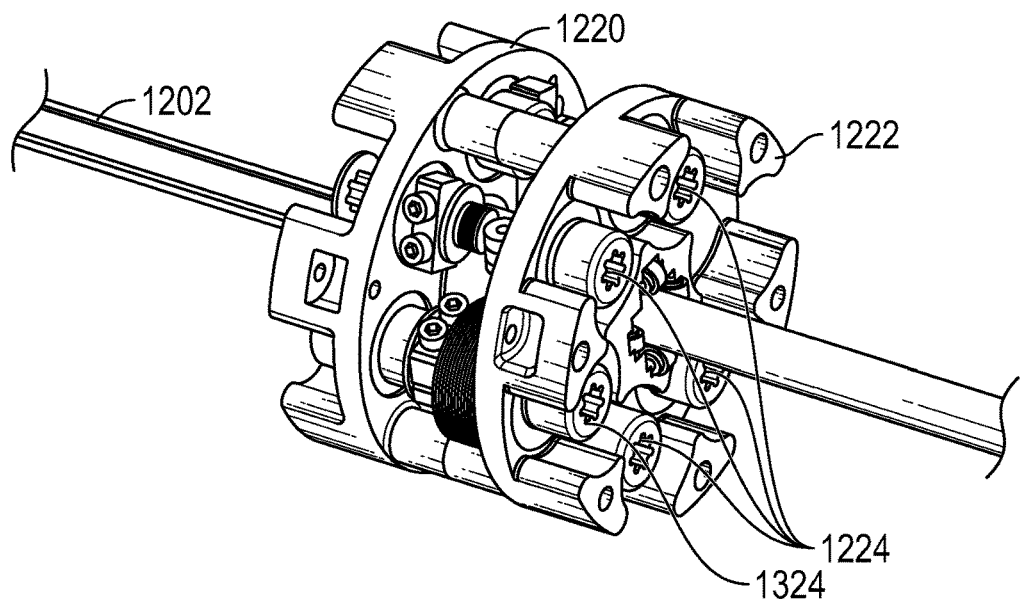
FIG. 23 illustrates a top perspective view of a handle and shaft of an instrument, according to one embodiment.

FIG. 23 illustrates a top perspective view of a handle and shaft of an instrument, according to one embodiment. The shaft 1202 is translatable relative to the handle 1220. From this view, one can see the one or more mechanical inputs 1224, which upon rotation, actuate the end effector. In addition, one can see the one or more mechanical inputs 1324, which upon rotate, allow for translation of the shaft 1202 relative to the handle 1220 along an axis of insertion. The attachment interface 1222 includes the one or more mechanical inputs 1224, 1324 e.g., receptacles, pulleys or spools, that are designed to reciprocally mate with one or more torque couplers 314 on an attachment interface 310 of the IDM 300 (shown in FIG. 3).

Figure 24A:
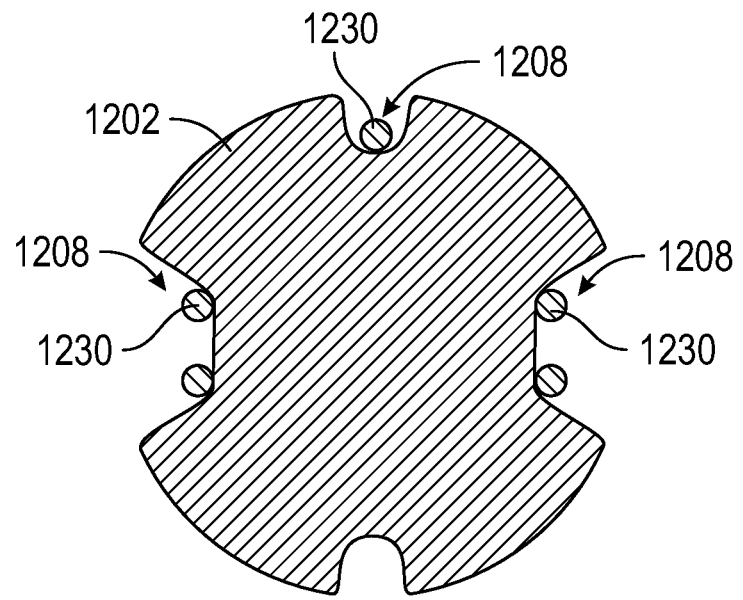
FIG. 24A illustrates a schematic view of a cross-section of an instrument shaft utilizing the insertion architecture shown in FIG. 12, according to one embodiment.
Figure 24B:
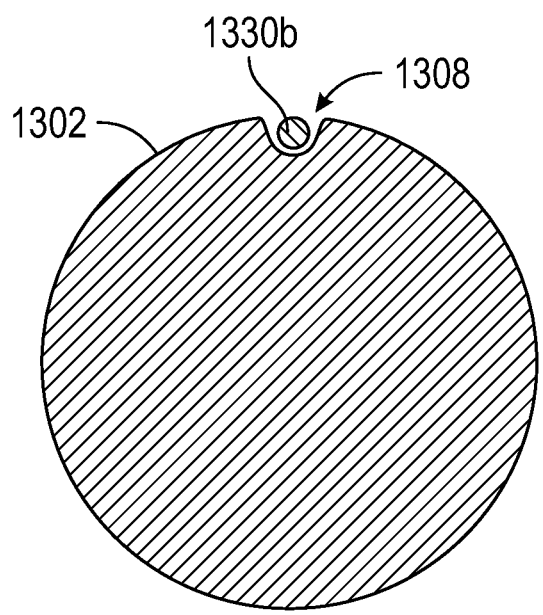
FIG. 24B illustrates a schematic view of a cross-section of an instrument shaft utilizing the insertion architecture shown in FIG. 21, according to one embodiment.

FIG. 24A illustrates a schematic view of a cross-section of an instrument shaft utilizing the insertion architecture shown in FIG. 12, while FIG. 24B illustrates a schematic view of a cross-section of an instrument shaft utilizing the alternative insertion architecture shown in FIG. 21. While not visible, each of the cross-sections in FIGS. 24A and 24B include openings or lumens that extend therethrough. As shown in FIG. 24A, the insertion architecture of FIG. 12 results in one or more cables 1230 that extend through grooves or channels 1208 that extend along an outer surface of the shaft 1202. In contrast, as shown in FIG. 24B, the insertion architecture of FIG. 21 results in one or more cables 1330*b* that extend through less grooves or channels 1308 (here a single channel) along an outer surface of the shaft 1202. This is because in the alternative architecture of FIG. 21, cables are more inclined to extend within the body of the shaft 1302. For example, there are no end effector cables on the outside of the shaft 1302. With less cables extending on the outside of the shaft 1302, the architecture in FIG. 21 can result in an overall smoother shaft surface with less grooves or channels extending on an outer surface.

VIII. Embodiments of Insertion Architectures for Specific Instruments

The architectures described above (e.g., shown in FIGS. 12 and 21) can be used to actuate an end effector and accommodate instrument insertion. In addition, these architectures can be incorporated into specific types of instruments to assist in surgical procedures.

Figure 25:
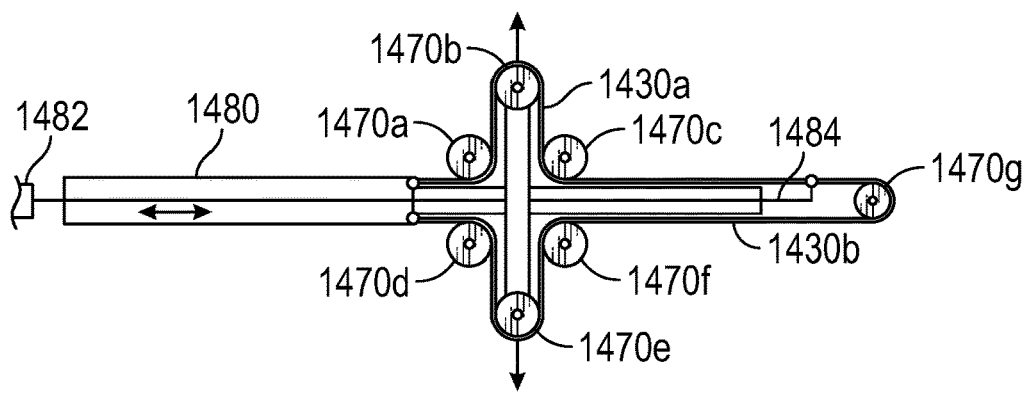
FIG. 25 illustrates a schematic diagram showing an architecture for driving a knife in a vessel sealer, according to one embodiment.
Figure 26:
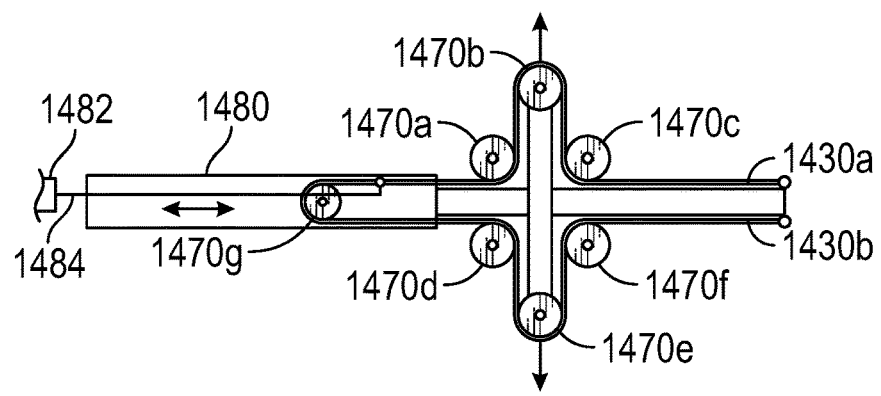
FIG. 26 illustrates a schematic diagram showing an alternative architecture for driving a knife in a vessel sealer, according to one embodiment.
Figure 27:
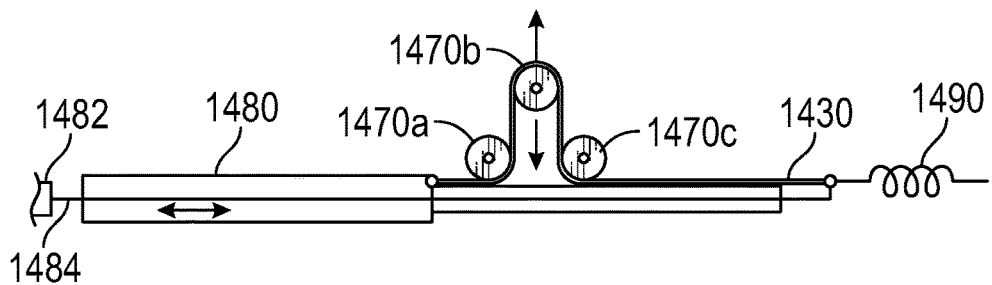
FIG. 27 illustrates a schematic diagram showing yet another alternative architecture for driving a knife in a vessel sealer, according to one embodiment.

One such instrument is a vessel sealer. With a vessel sealer, a knife or cutter can be driven through to cut tissue. In some embodiments, motion of the knife is rotational. In other embodiments, motion of the knife is translational. FIGS. 25-27 show different architectures that can be incorporated into a vessel sealer instrument to drive a knife through a vessel sealer. The architectures shown in these figures are like the architecture and related mechanisms shown in FIG. 12, but in other embodiments, the architectures can be like the architecture and related mechanisms shown in FIG. 21.

FIGS. 25-27 illustrate schematic diagrams showing different architectures for driving a knife in a vessel sealer. The architectures create a differential in path length amongst cables, and turns this differential path length change into linear motion of the knife. In the embodiments in FIGS. 25 and 26, two cables 1430*a*, 1430*b* are placed in counter tension, while in the embodiment in FIG. 27, a single cable 1430 and spring 1490 is used for counter tension. In the embodiments where two cables are placed in counter tension, linear motion of the knife is achieved by having both differentials on the same input axis, but in opposite directions (e.g., one is unwrapping cable while the other is wrapping cable). The dual, opposing cable approach also utilizes a redirect pulley to close the tension loop, and this can be mounted at or near a proximal end or at or near a distal end of a shaft (shown respectively in FIGS. 25 and 26). Once you have cable that is being pulled in and out, the knife can be coupled to a section of cable to create an in and out motion of the knife.

FIG. 25 illustrates a schematic diagram showing an architecture for driving a knife 1482 in a vessel sealer 1480. The architecture comprises a first cable 1430*a* and a second cable 1430*b*, wherein the first cable 1430*a* and second cable 1430*b* are in counter tension. The architecture further comprises one or more spools or pulley members 1470*a*, 1470*b*, 1470*c* that are engaged by the first cable 1430*a*, and one or more spools or pulley members 1470*d*, 1470*e*, 1470*f* that are engaged by the second cable 1430*b*, and a redirect spool or pulley 1470*g* that closes the tension loop. The redirect pulley 1470*g* is positioned at or near a proximal portion of the shaft. With the first cable 1430*a* and second cable 1430*b* in counter tension to one another, the knife 1482 can be coupled to a section of cable (e.g., first cable 1430*a*) via a connector such as elongate member 1484, thereby creating an in and out motion of the knife 1482 relative to the vessel sealer 1480. In some embodiments, elongate member 1484 comprises a push rod. In other embodiments, elongate member 1484 withstands the driving compression forces without buckling.

FIG. 26 illustrates a schematic diagram showing an alternative architecture for driving a knife in a vessel sealer. The architecture is similar to that shown in FIG. 25; however, in the present embodiment, the redirect pulley is positioned at or near a distal portion of the shaft.

FIG. 27 illustrates a schematic diagram showing yet another alternative architecture for driving a knife in a vessel sealer. Unlike the prior embodiments in FIGS. 25 and 26, the architecture in the present embodiment utilizes a single cable 1430 that is in counter tension with a spring 1490. The architecture further comprises one or more spools or pulley members 1470*a*, 1470*b*, 1470*c* that are engaged by the first cable 1430*a*. With the cable 1430 in counter tension with the spring 1490, the knife 1482 can be coupled to a section of the cable 1430, thereby creating an in and out motion of the knife 1482 relative to the vessel sealer 1480.

Another device that can serve as an insertion instrument is a camera. The camera can be used for endoscopic surgery. The architecture can vary depending on whether the camera is a rigid camera or an articulating camera, for which actuation for articulation will have to be provided.

Figure 28:
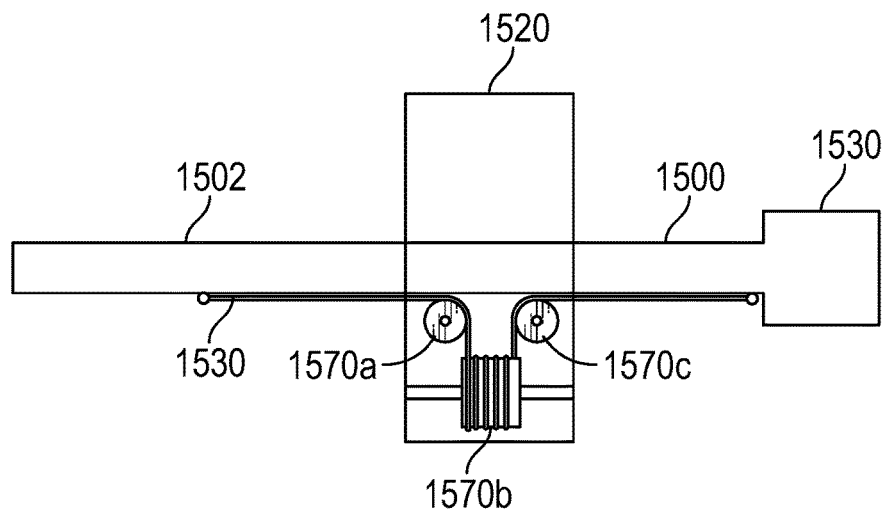
FIG. 28 illustrates a schematic diagram showing an architecture for making a rigid camera an insertion instrument, according to one embodiment.

FIG. 28 illustrates a schematic diagram showing an architecture for making a rigid camera an insertion instrument. The camera 1500 comprises a distal image payload connected by a shaft 1502 to a camera handle 1530 which has interface buttons and a cable coming out of it. The cable 1530 is received in a channel or groove formed on the outside of the shaft 1502, while the insertion handle 1520 is positioned around the shaft 1502. This in effect adds a second handle to the endoscope which enables insertion capability. The cable 1530 extends through one or more spools 1570*a*, 1570*b*, 1570*c*. In the present embodiment, spool 1570*b* can be a capstan. In some embodiments, the capstan can comprise a zero-walk capstan (as shown in FIG. 17), while in other embodiments, the capstan can allow cable walk (as shown in FIGS. 18 and 19). Via the capstan mechanism, the camera is capable of translation along an axis of insertion. In some embodiments, the core payload maintains the same sealing architecture as a rigid scope, so it can be expected to be sterilized with the same methods. For a rigid scope, this means it can be autoclaved. The additional insertion handle 1520 may also look like an instrument from a sterilization perspective and can be autoclaved as well.

While FIG. 28 shows an architecture for making a rigid camera an insertion instrument, articulating cameras present additional complexity, as mechanisms would be added to the camera to provide for articulation. For the articulating camera, one or more cables (e.g., actuation or wrist cables) can be provided to accommodate articulating movement. The camera can also be housed in a sealed area, such that if one is to run the one or more cables on the outside, one can also create a sealed compartment for the camera that excludes the one or more cables. With this architecture, it may be possible that some particles and debris get into small spaces within the sealed area. In some embodiments, to prevent the contamination, one solution may be to add two articulation motors within the sealed camera area rather than relying on the IDM for articulation motion. This greatly simplifies the cleaning and sealing of the camera components by taking the cables from the outside of the tube and putting them in the sealed inside. Another benefit of adding the two articulation motors within the sealed camera is that articulation of the camera can be controlled as soon as the camera is plugged into a vision box. This enables features like keeping the camera straight during installation or removal and being able to articulate the camera from the camera handle to look around during off-robot use. This then makes the articulation camera look a lot like the rigid camera from a sterilization perspective such that it is possible to be autoclaved.

Figure 29:
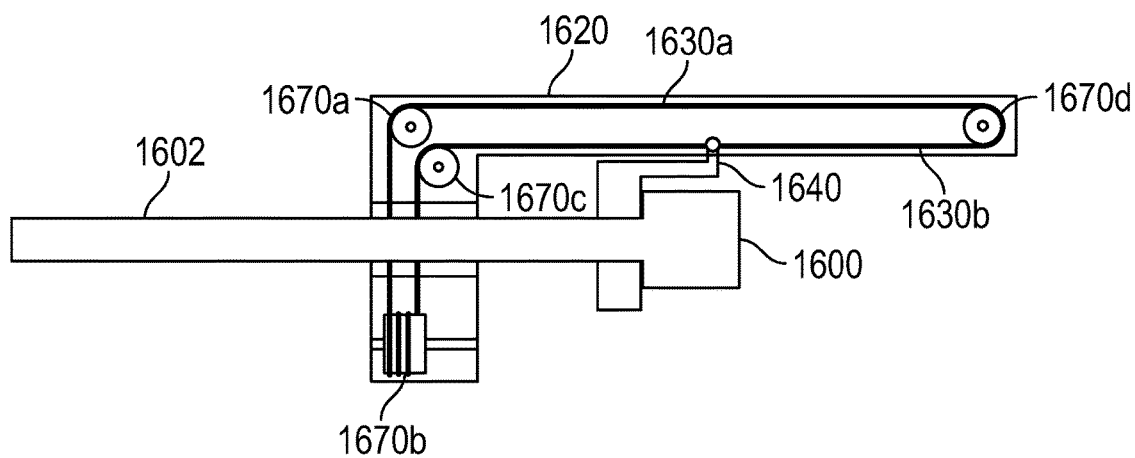
FIG. 29 shows a first insertion architecture that allows a camera to be separated from an insertion handle, according to one embodiment.

If a camera is not able to be autoclaved, then the sealed camera core and the insertion section may need to be separated for cleaning and insertion. This is because it is desirable to autoclave an insertion handle to achieve reliable sterilization. FIG. 29 shows a first insertion architecture that allows a camera to be separated from an insertion handle, while FIGS. 30 and 31 show a second insertion architecture that allows a camera to be separated from an insertion handle, thereby allowing for better sterilization.

FIG. 29 shows a first insertion architecture that allows a camera to be separated from an insertion handle. The architecture has an autoclavable insertion handle 1620 that latches onto an IDM and is separable from the camera core 1600. The camera core 1600 comprises a shaft 1602 that extends through the handle 1620. The handle 1620 comprises one or more wires 1630*a*, 1630*b* that extend through spools 1670*a*, 1670*b*, 1670*c*, 1670*d*. In the present embodiment, spool 1670*b* comprises a capstan. In some embodiments, the spool 1670*b* comprises a leadscrew. In some embodiments, the capstan is a zero-walk capstan (as shown in FIG. 17), while in other embodiments, the capstan allows cable walk. The insertion handle 1620 can be removably attached to the camera core 1600 via a connector 1640. In some embodiments, the connector 1640 comprises a bracket. In other embodiments, the connector 1640 comprises a vertical plate that the camera latches to. As the insertion handle 1620 is removably attached to the camera core 1600, each is capable of separation for cleaning.

Figure 30:
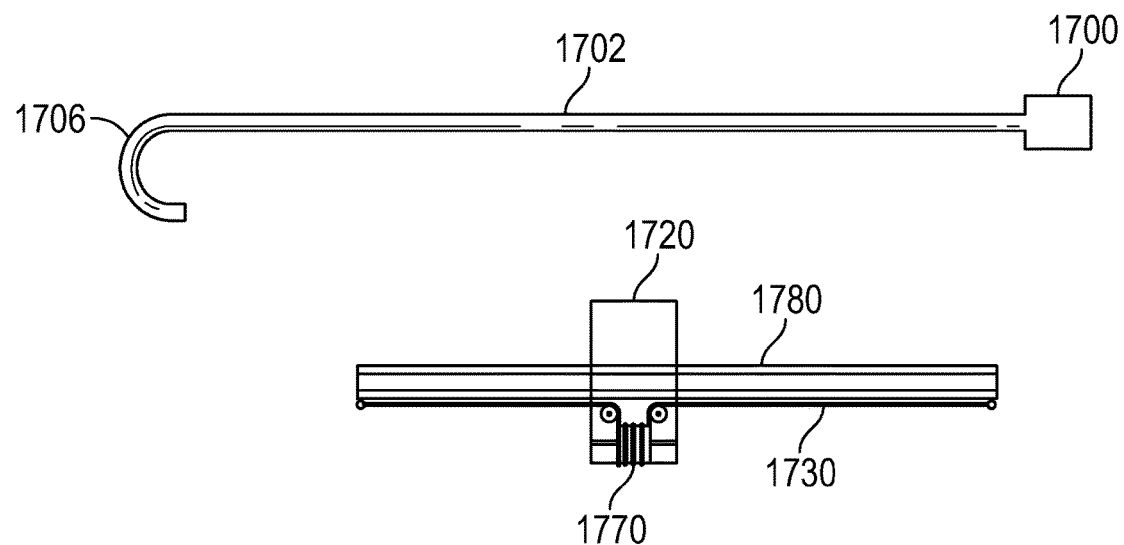
FIGS. 30 and 31 show a second insertion architecture that allows a camera to be separated from an insertion handle, according to one embodiment.
Figure 31:
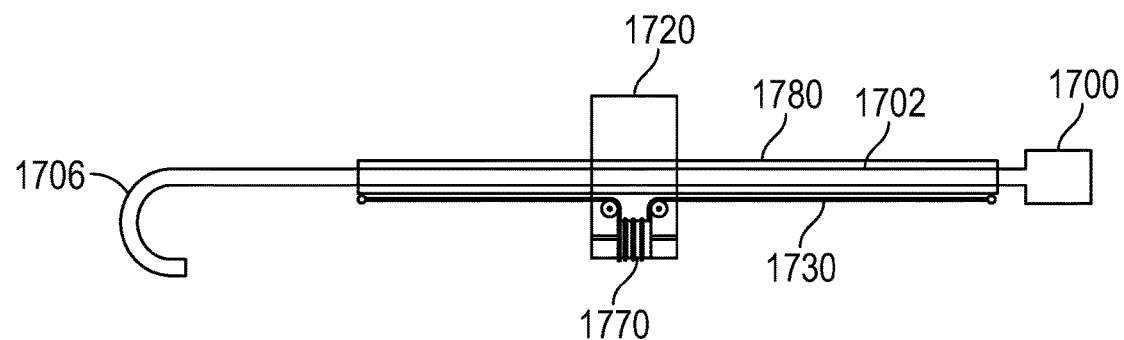

FIGS. 30 and 31 show a second architecture that allows a camera to be separated from an insertion handle. In the present embodiment, an overtube 1780 is provided that has an insertion cable 1730 attached to it and through which a camera 1700 can be loaded for a procedure. FIG. 30 shows the camera 1700 detached and separated from the overtube 1780, while FIG. 31 shows the camera 1700 loaded into the overtube 1780. To load the camera 1700 into the overtube, a distal tip 1706 and shaft 1702 of the camera 1700 passes through the overtube 1780. The overtube 1780 is connected to a handle 1720 which houses a spool 1770 in the form of a capstan. This architecture has the benefit of keeping the camera 1700 separate from an insertion handle 1720 if desired, so that both components can be easily cleaned. Furthermore, the camera 1700 is kept low profile in use, as it is to be fit into the overtube 1780. As the insertion handle 1720 is removably attached to the camera core 1700, each is capable of separation for cleaning.

Figure 32:
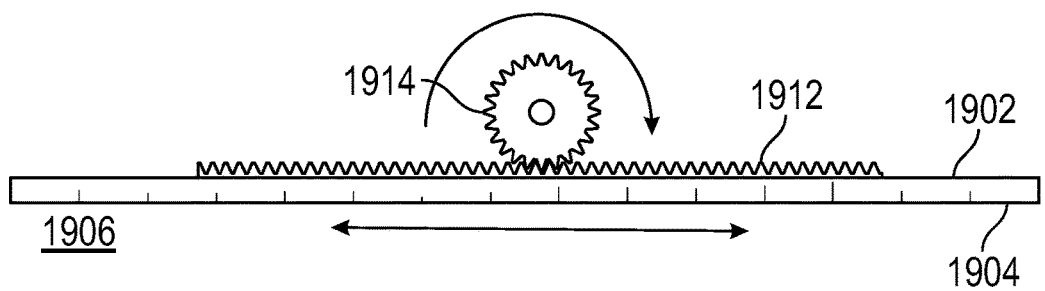
FIG. 32 illustrates a diagram showing an alternative architecture for shaft translation, according to another embodiment.

FIG. 32 illustrates a diagram showing an alternative architecture for shaft translation, according to another embodiment. In the present embodiment, the instrument comprises a shaft 1902 having a proximal portion 1904 and a distal portion 1906. Insertion of the shaft 1902 can be driven by a rack gear 1912 and pinion 1914, wherein rotation of the pinion 1914 results in translation of the rack gear 1912 and the shaft 1902 that is coupled to the rack gear 1912. In some embodiments, the rack gear 1912 is positioned on the instrument shaft 1902, while the pinion 1914 is positioned within the housing of the instrument handle. A motor driver can be used to translate the shaft 1902 relative to the handle. In some embodiments, a spur gear can be used, in addition to a cycloid pin rack profile. In some embodiments, the rack gear 1912 and pinion 1914 can be used on its own to cause insertion or translation of the shaft 1902. In other embodiments, the rack gear 1912 and pinion 1914 can accompany and complement any of the insertion mechanisms described above. The rack gear 1912 and pinion 1914 can be used with any of the types of instruments described above to provide linear insertion of the instrument shaft relative to the handle.

IX. Surgical Tool Sealing

When performing surgical procedures, such as laparoscopic procedures, surgeons use insufflation. This means that cannulas inserted into a patient are sealed against the surgical tool shafts to maintain positive pressure inside a patient's body. Seals can be coupled to the surgical tool shafts to prevent air from leaking from a patient's body. These seals are often designed to accommodate tools having round cross-sections. It can be difficult to apply the same seals to tools having non-circular shapes and concave features on the outer surfaces of the shaft, as passages formed by these surfaces can allow the release of air pressure at the tool seal. For example, instruments having instrument based insertion architectures can have cross-sections (as shown in FIG. 24A) with grooves 1208 where air can leak from a patient.

To address this challenge, a system including multiple seals can be provided to prevent air leakage in a patient. In particular, a novel seal can be provided that works with a cannula seal having a circular outer shape, which is customary with instruments having circular cross-sections. The novel seal can pass through the circular cannula seal, thereby providing a consistent rotary seal. The novel seal would advantageously discretize any rotary and linear motion to create two boundaries at which a seal is created. The discretization is achieved by having an intermediate tool seal piece.

Figure 33:
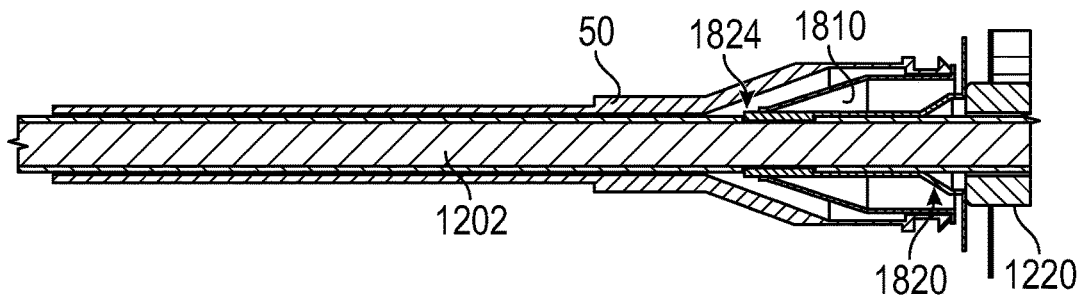
FIG. 33 shows a side cross-sectional view of an instrument having multiple seals to prevent air leakage from a patient.
Figure 34:
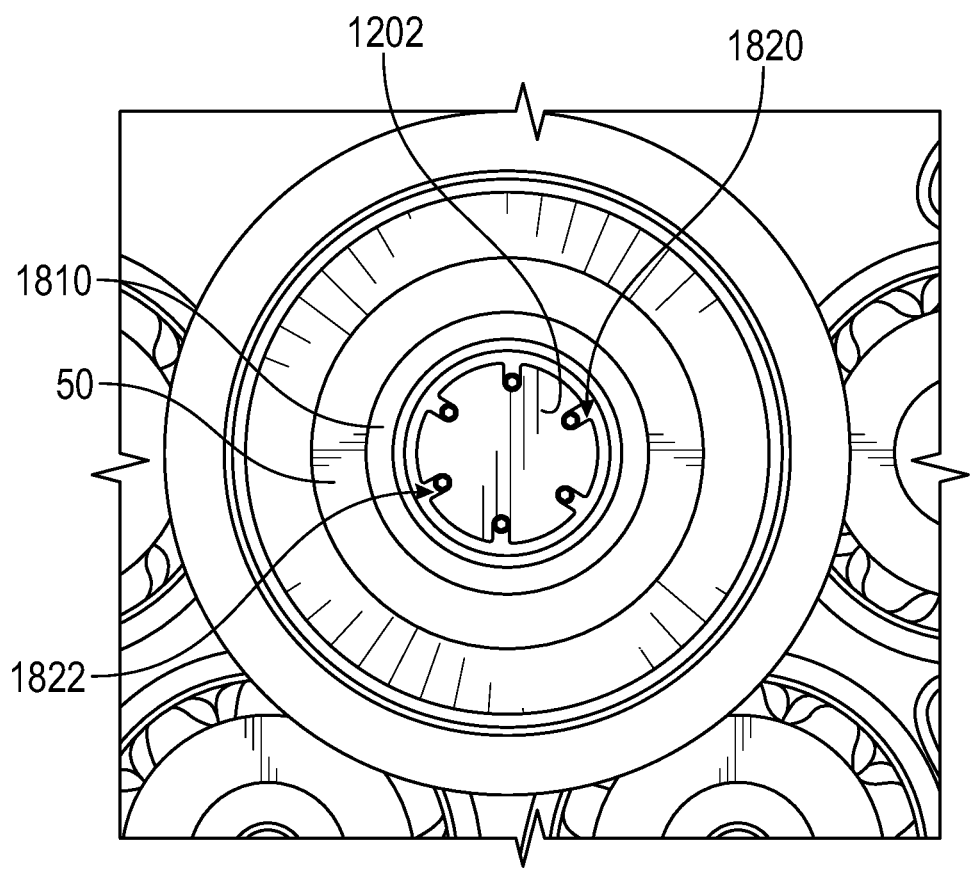
FIG. 34 shows a front cross-sectional view of the instrument having the multiple seals.

FIG. 33 shows a side cross-sectional view of an instrument having multiple seals to prevent air leakage from a patient. FIG. 34 shows a front cross-sectional view of the instrument having the multiple seals. The instrument 1200 is inserted into a cannula 50, and is akin to the instrument shown in FIG. 11 having an instrument based insertion architecture. The instrument can include a shaft 1202 translatable relative to a handle 1220. The shaft 1202 can have one or more channels or grooves 1208 extending along an outer surface thereof, thereby creating passages that could allow air to leak from a patient.

To prevent air leakage, a multi-seal system advantageously couples to the instrument. In some embodiments, the multi-seal system comprises a first seal 1810 and a second seal 1820 that can work in conjunction to reduce the risk of air leakage. In some embodiments, the first seal 1810 and second seal 1820 are coaxial. As shown in FIG. 32, the second seal 1820 can be received in an interior of the first seal 1810. The first seal 1810 can have a cross-section having a round outer perimeter and round inner perimeter, while the second seal 1820 can have a cross-section having a round outer perimeter and an inner perimeter with inner protrusions, tabs or nubs 1822, as shown in FIG. 34. The advantage of having a second seal 1820 with the inner protrusions is that the inner protrusions can fill in voids, such as grooves 1208, that may extend along an outside of the instrument shaft 1202, thereby reducing the risk of air leakage from a patient during surgery.

The multi-seal advantageously discretizes rotary and linear motion to create two boundaries at which a seal is created. The second seal 1820, with its inner protrusions 1822, can slide down the outer grooves of the instrument shaft 1202, thereby creating a sliding linear seal for instrument shaft motion. One skilled in the art will appreciate that while the second seal 1820 is shown with a plurality of inner protrusions that are rounded and spaced substantially symmetrically around an inner perimeter, the inner portion of the second seal 1820 can assume other shapes as well, so long as the molding process substantially matches the interior of the second seal 1820 to the outer surface of the instrument shaft 1202. When received in the grooves 1208 of the instrument 1200, each of the inner nubs 1822 of the second seal 1820 creates a rotary seal point 1824. These rotary seal points allow the instrument 1200 and second seal 1820 to rotationally lock and rotate together upon rotation of the instrument shaft 1202. While the present embodiment shows a multi-seal having dual seals, in other embodiments, three, four, or more seals can work together to reduce the risk of air leakage from a patient during surgery.

X. Alternative Considerations

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context unless otherwise explicitly stated.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

What is claimed is:

1. A medical device comprising:
   a shaft comprising a proximal portion and a distal portion;
   an end effector connected to the distal portion of the shaft; and
   a handle coupled to the shaft, wherein the handle includes a first mechanical input and a second mechanical input, wherein the first mechanical input is configured to cause actuation of the end effector, and the second mechanical input is configured to cause translation of the shaft relative to the handle.

2. The medical device of claim 1, wherein the actuation of the end effector is performed via a first actuation mechanism that is decoupled from a second actuation mechanism that causes the translation of the shaft relative to the handle.

3. The medical device of claim 2, wherein the first actuation mechanism includes a first cable that extends through a first set of pulleys, wherein manipulation of at least one pulley of the first set of pulleys via the first mechanical input causes a change of length of the first cable within the handle, thereby causing actuation of the end effector.

4. The medical device of claim 3, wherein the second actuation mechanism includes a second cable that engages a spool, wherein manipulation of the spool via the second mechanical input causes the shaft to translate relative to the handle.

5. The medical device of claim 4, wherein the change of length of the first cable within the handle to cause actuation of the end effector is not affected by the second actuation mechanism that translates the shaft relative to the handle.

6. The medical device of claim 3, wherein the first cable of the first actuation mechanism extends from the proximal portion of the shaft, through the first set of pulleys and to the distal portion of the shaft.

7. The medical device of claim 6, wherein manipulation of the at least one pulley of the first set of pulleys to cause a change of length of the first cable within the handle comprises linear or rotary motion of the at least one pulley.

8. The medical device of claim 4, wherein the spool comprises a capstan.

9. The medical device of claim 8, wherein the capstan comprises a zero-walk capstan.

10. The medical device of claim 8, wherein rotation of the second mechanical input causes rotation of the capstan.

11. The medical device of claim 2, wherein the first actuation mechanism includes one or more cables that extend through a first set of pulleys, and the second actuation mechanism includes one or more cables and an insertion spool, wherein at least one of the one or more cables of the first actuation mechanism terminates on the insertion spool.

12. The medical device of claim 11, wherein the one or more cables of the first actuation mechanism comprise end effector cables and the one or more cables of the second actuation mechanism comprise insertion cables.

13. The medical device of claim 11, wherein rotation of the second mechanical input causes rotation of the insertion spool thereby causing translation of the shaft relative to the handle.

14. The medical device of claim 12, wherein the one or more cables of the second actuation mechanism are wound by the insertion spool during translation of the shaft relative to the handle, and wherein the one or more cables of the first actuation mechanism are unwound by the insertion spool during translation of the shaft relative to the handle, wherein a length of the one or more cables that are wound by the insertion spool is substantially counterbalanced by the one or more cables being unwound.

15. A medical system comprising:
   a base;
   a tool holder coupled to the base, the tool holder including an attachment interface; and
   an instrument, wherein the instrument comprises:
      a shaft comprising a proximal portion and a distal portion,
      an end effector extending from the distal portion of the shaft, and
      a handle coupled to the shaft, the handle including a reciprocal interface releasably attachable to the attachment interface, a first mechanical input, and a second mechanical input, wherein the first mechanical input is configured to cause actuation of the end effector, and the second mechanical input is configured to cause translation of the shaft relative to the handle.

16. The medical system of claim 15, further comprising a robotic arm between the base and tool holder.

17. The medical system of claim 16, wherein the actuation of the end effector is performed via a first actuation mechanism that is decoupled from a second actuation mechanism that causes the translation of the shaft relative to the handle.

18. The medical system of claim 17, wherein the first actuation mechanism includes a first cable that extends through a first set of pulleys, wherein manipulation of at least one pulley of the first set of pulleys via the first mechanical input causes a change of length of the first cable within the handle, thereby causing actuation of the end effector, and wherein the translation of the shaft relative to the handle is performed via the second actuation mechanism that includes a second cable that engages a spool, wherein manipulation of the spool via the second mechanical input causes the shaft to translate relative to the handle.

19. The medical system of claim 18, wherein the change of length of the first cable within the handle to cause actuation of the end effector is not affected by the second actuation mechanism that translates the shaft relative to the handle.

20. The medical system of claim 19, wherein manipulation of the at least one pulley of the first set of pulleys to cause a change of length of the first cable within the handle comprises linear or rotary motion of the at least one pulley.

21. A surgical method comprising:
providing an instrument capable of delivery through an incision or natural orifice of a patient to perform a procedure at a surgical site, wherein the instrument comprises:
a shaft including a proximal portion and a distal portion;
a handle coupled to the shaft; and
an end effector extending from the distal portion of the shaft,
wherein the shaft is capable of translation relative to the handle.

22. The surgical method of claim 21, wherein the instrument includes a first actuation mechanism for actuating the end effector and a second actuation mechanism for translating the shaft relative to the handle, wherein the first actuation mechanism comprises a first set of pulleys and a first cable and the second actuation mechanism comprises a spool and a second cable.

23. The surgical method of claim 22, further comprising manipulating the end effector via the first actuation mechanism.

24. The surgical method of claim 23, further comprising translating the shaft via the second actuation mechanism, wherein the first actuation mechanism is decoupled from the second actuation mechanism.

25. A surgical method comprising:
delivering an instrument through an incision or natural orifice of a patient to perform a procedure at a surgical site, wherein the instrument comprises:
a shaft including a proximal portion and a distal portion;
a handle coupled to the shaft; and
an end effector extending from the distal portion of the shaft,
wherein the shaft is capable of translation relative to the handle.

26. The surgical method of claim 25, wherein the instrument includes a first actuation mechanism for actuating the end effector and a second actuation mechanism for translating the shaft relative to the handle, wherein the first actuation mechanism comprises a first set of pulleys and a first cable and the second actuation mechanism comprises a spool and a second cable.

27. The surgical method of claim 26, further comprising manipulating the end effector via the first actuation mechanism.

* * * * *